United States Patent
Paulsen et al.

(10) Patent No.: US 10,228,335 B2
(45) Date of Patent: *Mar. 12, 2019

(54) METHOD FOR NUCLEAR MAGNETIC RESONANCE DIFFUSION MEASUREMENTS

(71) Applicant: SCHLUMBERGER TECHNOLOGY CORPORATION, Sugar Land, TX (US)

(72) Inventors: Jeffrey Paulsen, Brookline, MA (US); Yi-Qiao Song, Newton Center, MA (US)

(73) Assignee: Schlumberger Technology Corporation, Sugar Land, TX (US)

( * ) Notice: Subject to any disclaimer, the term of this patent is extended or adjusted under 35 U.S.C. 154(b) by 893 days.

This patent is subject to a terminal disclaimer.

(21) Appl. No.: 14/586,376

(22) Filed: Dec. 30, 2014

(65) Prior Publication Data

US 2015/0153433 A1 Jun. 4, 2015

Related U.S. Application Data

(63) Continuation-in-part of application No. 13/958,820, filed on Aug. 5, 2013, now Pat. No. 9,541,513.
(Continued)

(51) Int. Cl.
  *G01N 24/08* (2006.01)
  *G01R 33/44* (2006.01)
  (Continued)

(52) U.S. Cl.
  CPC ......... *G01N 24/081* (2013.01); *G01R 33/448* (2013.01); *G01R 33/56341* (2013.01); *G01V 3/32* (2013.01)

(58) Field of Classification Search
  CPC ............ G01R 33/448; G01R 33/56341; G01N 24/081; G01V 3/32
  See application file for complete search history.

(56) References Cited

U.S. PATENT DOCUMENTS

| 6,842,000 B2 * | 1/2005 | Norris .............. G01R 33/56509 324/309 |
| 7,541,809 B2 * | 6/2009 | Miyoshi ................ A61B 5/055 324/306 |

(Continued)

FOREIGN PATENT DOCUMENTS

| WO | WO9209901 A1 | 6/1992 |
| WO | WO2007087494 A2 | 8/2007 |

OTHER PUBLICATIONS

Blumler, et al., "Chapter 54: Review: NMR Detection and Characterization of Hydrocarbons in Subsurface Earth Formations", Spatially Resolved Magnetic Resonance: Methods, Materials, Medicine, Biology, Rheology, Geology, Ecology, Hardware, Dec. 20, 2007.
(Continued)

*Primary Examiner* — Dixomara Vargas

(57) ABSTRACT

A method and system for determining a property of a substance using nuclear magnetic resonance (NMR) is described herein. The method includes applying a NMR pulse sequence to the substance. The NMR pulse sequence includes a first set of pulses and a second set of pulses. The first set of pulses and the second set of pulses encode for overlapping diffusion times. By overlapping diffusion times, the NMR pulse sequence can be used to measure a diffusion coefficient for a first diffusion time, a diffusion coefficient for a second diffusion time, and a correlation between the two overlapping diffusion times. This information, in turn, can be used to differentiate between intrinsic bulk diffusivity of the substance and the reduced diffusivity of the substance caused by restricted diffusion.

20 Claims, 27 Drawing Sheets

Related U.S. Application Data

(60) Provisional application No. 61/748,704, filed on Jan. 3, 2013.

(51) Int. Cl.
  *G01R 33/563* (2006.01)
  *G01V 3/32* (2006.01)

(56) References Cited

U.S. PATENT DOCUMENTS

| | | | |
|---|---|---|---|
| 9,541,513 B2* | 1/2017 | Paulsen | G01N 24/081 |
| 2004/0189296 A1 | 9/2004 | Sun et al. | |
| 2005/0007100 A1 | 1/2005 | Basser et al. | |
| 2010/0033182 A1* | 2/2010 | Ozarslan | G01R 33/44 |
| | | | 324/309 |

OTHER PUBLICATIONS

Callaghan, et al., "Diffusion-diffusion correlation and exchange as a signature for local order and dynamics", Journal of Chemical Physics, vol. 120, Feb. 20, 2004, pp. 4032-4038.

Callaghan, et al., "Velocity Exchange Spectroscopy", Journal of Magnetic Resonance, Series A, vol. 106, Issue 2, Feb. 1994, pp. 260-265.

Chen, et al., "Quantitative NMR imaging of multiphase flow in porous media", Magnetic Resonance Imaging, vol. 10, No. 5, 1992, pp. 815-826.

Cheng, et al., "Multiple Scattering by NMR", Journal of the American Chemical Society, vol. 121, Aug. 14, 1999, pp. 7935-7936.

Grebenkov, D. S., "NMR survey of reflected Brownian motion", Reviews of Modern Physics, 2007, 79(3), pp. 1077-1137.

Hurlimann, et al., "Experimental Investigation of Split- 180 Sequences", date unavailable, pp. 1-32.

Hurlimann, et al., "Hydrocarbon Composition From NMR Diffusion and Relaxation Data", Petrophysics, vol. 50, No. 2, 2009, pp. 116-129.

Jespersen, et al., "The displacement correlation tensor: Microstructure, ensemble anisotropy and curving fibers", Journal of Magnetic Resonance, vol. 208, Issue 1, Jan. 2011, pp. 34-43.

Jespersen, S. J. "Equivalence of double and single wave diffusion contrast at low diffusion weighting", NMR in Biomedicine, 2011, 25, pp. 813-818.

Kuder, T. A. et al., "Diffusion Pore Imaging by Hyperpolarized Xenon-129 Nuclear Magnetic Resonance", Physical Review Letters, 2013, 111(2), pp. 028101.

Latour et al., "Time-Dependent Diffusion Coefficient of Fluids in Porous Media as a Probe of Surface-to-vol. Ratio", Journal of Magnetic Resonance, Series A, 1993, 101(3), pp. 342-346.

Lawrenz, et al., "A tensor model and measures of microscopic anisotropy for double-wave-vector diffusion-weighting experiments with long mixing times", Journal of Magnetic Resonance, vol. 202, Issue 1, Jan. 2010, pp. 43-56.

Mitra, et al, "Short-time behavior of the diffusion coefficient as a geometrical probe of porous media", Physical Review B., 1993, 47(14), pp. 8565-8574.

Mitra, Partha P., "Multiple wave-vector extensions of the NMR pulsed-field-gradient spin-echo diffusion measurement", Physical Review B., vol. 51, Jun. 1, 1995, pp. 15074-15078.

Ozarslan, et al., "Microscopic anisotropy revealed by NMR double pulsed field gradient experiments with arbitrary timing parameters", Journal of Chemical Physics, vol. 128, No. 15, 2008, pp. 154511-1.

Parsons, et al., "Temporal Diffusion Spectroscopy: Theory and Implementation in Restricted Systems Using Oscillating Gradients", Magnetic Resonance in Medicine, 2006, 55, pp. 75-84.

Price, W. S., "Pulsed-Field Gradient Nuclear Magnetic Resonance as a Tool for Studying Translational Diffusion: Part II, Experimental Aspects", Concepts in Magnetic Resonance, 1998, 10(4), pp. 197-237.

Shemesh, N. et al., "Overcoming apparent Susceptibility-Induced Anisotropy (aSIA) by bipolar double-Pulsed-field-Gradient NMR", Journal of Magnetic Resonance, 2011, 212, pp. 362-369.

Song, Yi-Qiao, "Novel NMR techniques for porous media research", Cement and Concrete Research, vol. 37, Issue 3, Mar. 2007, pp. 325-328.

Stepisnik et al, "Spectral characterization of diffusion in porous media by the modulated gradient spin echo with CPMG sequence", Journal of Magnetic Resonance, 2006, 182, pp. 195-199.

Xu, J. et al, "Sensitivity of MR Diffusion Measurements to Variations in Intracellular Structure: Effects of Nuclear Size", Magnetic Resonance in Medicine, 2009, 61(4), pp. 828-833.

Zheng, G. et al., "Suppression of Background Gradients in (B0 Gradient-Based) NMR Diffusion Experiments", Concepts in Magnetic Resonance, 2007, 30A(5), pp. 261-277.

Zielinski, et al., "Combined effects of diffusion, nonuniform-gradient magnetic fields, and restriction on an arbitrary coherence pathway", Journal of Chemical Physics, vol. 119, 2003, pp. 1093-1104.

Search Report and Written Opinion of International Patent Application No. PCT/US2013/073652 (IS12.3481) dated Dec. 6, 2013, 6 pages.

* cited by examiner

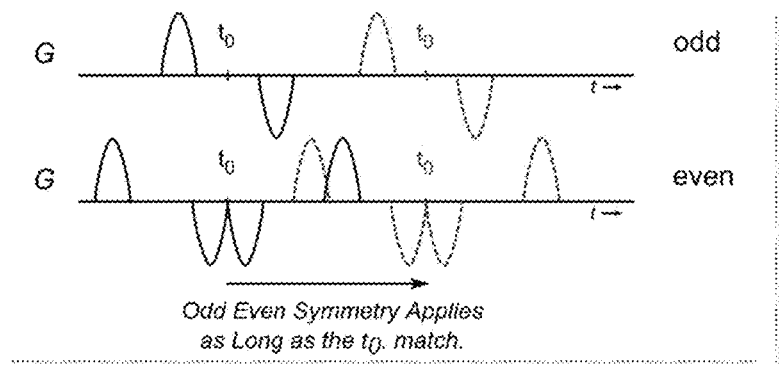
FIG. 28
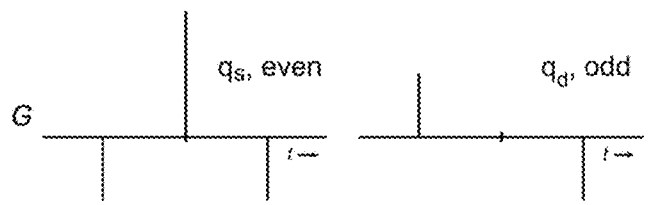
FIG. 29A
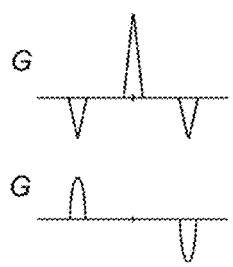 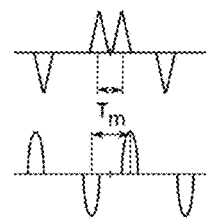 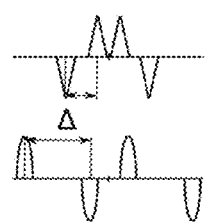
FIG. 29B　　　FIG. 29C　　　FIG. 29D

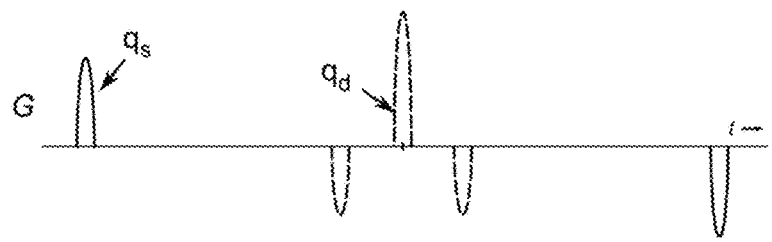
FIG. 29E
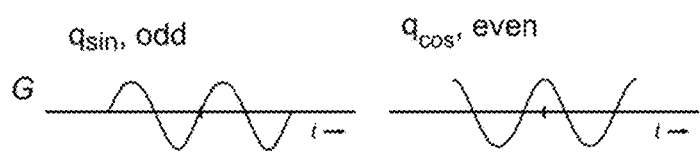
FIG. 30A
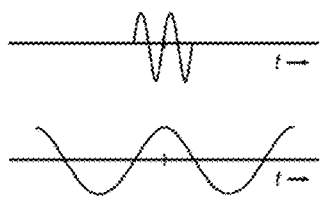 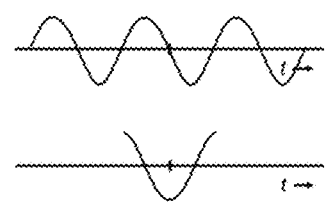
FIG. 30B          FIG. 30C

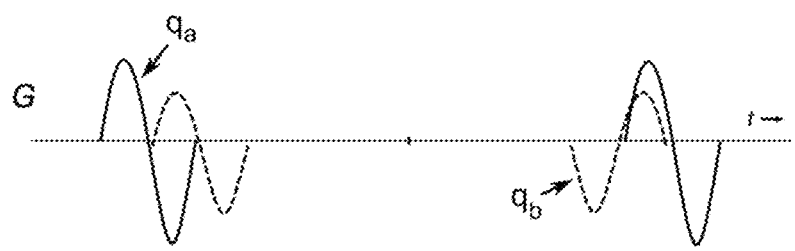
FIG. 30D
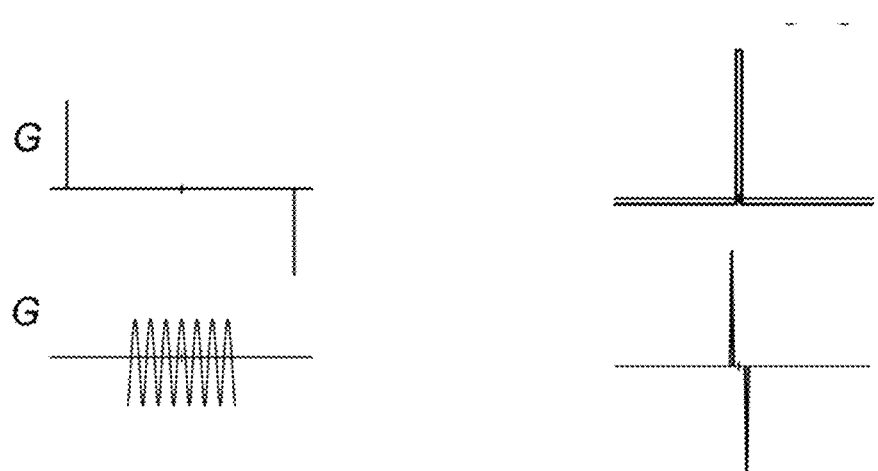
FIG. 31A
FIG. 31B
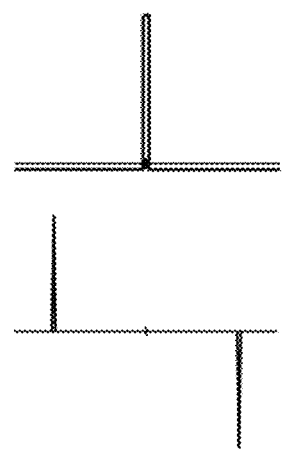
FIG. 31C

METHOD FOR NUCLEAR MAGNETIC RESONANCE DIFFUSION MEASUREMENTS

CROSS-REFERENCE TO RELATED APPLICATIONS

The present application is a continuation-in-part of U.S. patent application Ser. No. 13/958,820, filed on Aug. 5, 2013, which is incorporated herein by reference in its entirety, and which claims the benefit of U.S. Provisional Patent Application Ser. No. 61/748,704, filed Jan. 3, 2013, which is incorporated herein by reference in its entirety.

TECHNICAL FIELD

This disclosure relates to nuclear magnetic resonance (NMR) and, in particular, NMR diffusion measurements.

BACKGROUND

Nuclear magnetic resonance (NMR) can be used to determine properties of a substance. An NMR method includes applying a static magnetic field to the substance. The static magnetic field generates an initial magnetization of atomic nuclei within the substance. Then, an oscillating magnetic field is applied at a particular frequency to the substance. The oscillating field is composed of a sequence of radio frequency (RF) pulses that tip the magnetization of the atomic nuclei away from the initial magnetization. The sequence of pulses can be arranged so that the pulses and the static field interact with the nuclei to produce a NMR signal composed of "echoes" within at least a portion of the substance. The NMR signal is detected and can be used to determine properties of the substance.

In the oil and gas field industry, NMR is used to investigate the properties of subterranean formations and fluids within the formations. The formation is a porous medium and the fluids (e.g., water, oil and/or gas) within formations are contained within pore volumes of the formation. At least three different NMR measurements can be used to determine properties of a porous medium and a fluid contained therein: (i) a measurement of the absolute signal intensity of the NMR signal, (ii) a measurement of NMR signal relaxation and (iii) a measurement of diffusion. The relaxation measurement measures an inherent signal decay produced by atomic nuclei, whereas a diffusion measurement measures an additional decay produced by movement of the atomic nuclei. The absolute signal intensity can be used to determine the porosity of the porous medium. The relaxation measurement and diffusion measurement can be used to determine the pore size distribution of the porous medium and fluid type contained within the porous medium. For example, estimates of bound water, oil composition, and oil viscosity can be determined using relaxation measurements and diffusion measurements.

In particular, diffusion measurements are used to determine a diffusion coefficient of a fluid, which characterizes the distance that nuclei within the fluid will travel as a function of time. In an open or large volume, the diffusion coefficient of the fluid is known as a bulk diffusion coefficient. When the pore size within the formation is large, the measured diffusion coefficient will be similar to the bulk diffusion coefficient. However, in many cases, the pore size is small and this small pore size reduces the measured diffusion coefficient by impeding the movement of the nuclei within the fluid. Diffusion that is impeded by small pore size is known as restricted diffusion.

Diffusion measurements and relaxation measurements will both depend on the mobility of nuclei in a large bulk volume and the impediment caused by collisions with pore surfaces. For example, a fluid with high viscosity will have a smaller diffusion coefficient and a shorter relaxation time. Similarly, a porous medium with a small pore size will also shorten the diffusion coefficient and the relaxation time for a fluid. As explained above, however, diffusion and relaxation are affected by different mechanisms. Relaxation time is based on the inherent signal decay produced by atomic nuclei, whereas the diffusion coefficient is based on movement of atomic nuclei. So while these measurements are often correlated, each measurement can yield unique information. For instance, bound water will have a shortened $T_2$ relaxation time distribution. This shortened $T_2$ relaxation time distribution may intersect the $T_2$ relaxation time distribution of viscous oil in a large pore. However, an apparent diffusion coefficient (e.g., measured diffusion coefficient) of oil will still be orders of magnitude smaller than the apparent diffusion coefficient for water.

Nonetheless, diffusion measurements can be complicated when pore sizes are small and when two or more different fluids are located within pore volumes of a porous medium. Past diffusion measurement techniques yield limited or ambiguous information, especially in complex samples (e.g., porous media with different types of fluid). When characterizing oil composition, especially in emulsions or tight oil wet pores, differentiating the effects of composition and pore size is greatly complicated because bulk oil intrinsically has a broadened distribution of diffusion and relaxation times due to its varied composition. For such reasons, past diffusion and relaxation measurement techniques cannot unambiguously differentiate between restricted diffusion and composition of the fluid.

One technique used in magnetic resonance imaging (MRI) to make diffusion measurements of fluids within porous medium is known as a pulsed field gradient (PFG). A PFG is a short, timed pulse with spatially dependent magnetic field intensity. A PFG method applies pulses of magnetic field gradients along multiple directions along with a corresponding NMR pulse sequence (with RF pulses) to achieve spatial resolution (e.g., often referred to as "encoding"). The PFG can be used to detect molecular diffusion in fluids and obtain diffusion coefficients. A PFG sequence includes a pair of PFG pulses of identical amplitude (g) and duration ($\delta$). These two PFG pulses are separated by a time period ($\Delta$) (referred to as diffusion time). FIG. 1 shows a related art PFG pulse sequence 100 that can be applied to a fluid within a porous medium (e.g., a sample). The sequence 100 includes an excitation pulse 102 (e.g., single 90-degree RF pulse) to rotate the spin magnetization of the nuclei within the fluid to the transverse plane. The excitation pulse 102 excites the spins of the nuclei for encoding and detection. A first gradient pulse 104 encodes the initial position of the nuclei as a phase imprinting a wave of magnetization across the fluid. Afterwards, the nuclei move due to diffusion over a diffusion time ($\Delta$), while retaining the initial encoded phase. A second gradient pulse 106 of negative amplitude re-encodes for the position of the nuclei, but with opposite phase such that the net signal phase of each nuclei is proportional to its displacement.

The pulse sequence can be modified to improve its application for various different samples. For example, FIG. 2 shows another related art PFG pulse sequence 200. The sequence 200 shown in FIG. 2 uses a spin echo RF sequence that has an excitation pulse 202 (a 90-degree pulse) for excitation and a refocusing pulse 204 (a 180-degree pulse)

for refocusing to generate an echo. Because of the use of the refocusing pulse, the corresponding gradient pulses 206 and 208 are of the same sign (either positive or negative). The pulse sequences shown in FIGS. 1 and 2 are often referred to as single-pulse field gradient (or s-PFG).

Each PFG pulse is defined by an area parameter (q), which is further defined in units of reciprocal distance (e.g., $mm^{-1}$). This reciprocal distance corresponds to a wavelength of a wave vector imprinted across the sample by the first pulse and refocused by the second pulse. The area parameter (q) can be determined according to the following relationship:

$$q = \gamma g \delta, \tag{1}$$

where $\gamma$ is the gyromagnetic ratio of the nuclei ($s^{-1}\ G^{-1}$), g is the amplitude of the gradient pulse (G/cm), and $\delta$ is the width (or duration) of the pulse (s).

The NMR signal that is generated by the PFG pulses exhibits a decay. This decay is represented by the following relationship:

$$E(q) = E(0)\exp(-D\Delta q^2), \tag{2}$$

where D is the diffusion coefficient of the fluid, $\Delta$ is the diffusion time, and E is NMR signal data obtained from the generated NMR signal (e.g., signal amplitude). According to equation 2, encoding for diffusion is characterized by the area parameter of the gradient pulses (q). To obtain a diffusion coefficient, a series of experiments with different values of area parameters (q) or diffusion times ($\Delta$) can be performed and the NMR signal data obtained from the experiments (E) is analyzed using equation 2 above.

FIG. 3 shows another example of a related art pulse sequence 300 that can be applied to a fluid within a porous medium. This pulse sequence 300 is often referred to as a double-pulsed-field-gradient (d-PFG). The d-PFG pulse sequence 300 includes an initial excitation pulse 302 that excites the spins of the nuclei within the fluid. The sequence 300 also includes two pairs of gradient pulses 304 ($q_1$) and 306 ($q_2$) that are separated by a mixing time ($T_m$). Each pair of gradient pulses 304, 306 encode for displacement by imprinting and refocusing a wave-vector spatially across the sample, after which the NMR signal produced by the sequence is acquired. The d-PFG pulse sequence 300 uses two diffusion periods ($\Delta_1$) and ($\Delta_2$) to obtain correlation of the diffusive displacement during and between these two diffusion times.

The d-PFG pulse sequences are applied a number of times while the area parameters ($q_1$) and ($q_2$) are held constant and a gradient angle ($\theta$) between the pairs of gradient pulses is varied. In various embodiments, the first pair 304 is applied along a single direction (e.g., x-axis) and the second pair 306 is applied along a different direction (e.g., y axis). As the d-PFG pulse sequences are applied, the second direction is varied and the gradient angle ($\theta$) between the pairs thus also varies. A plot of the NMR signal for different values of the gradient angle ($\theta$) can potentially show modulation due to time dependent diffusion and diffusion anisotropy. Although such d-PFG pulse sequences can potentially identify anisotropically shaped pores when the pores are distributed isotropically in a bulk porous medium, such d-PFG techniques are less effective for heterogeneous porous media.

In another example, the d-PFG pulse sequence can be applied to a fluid within a heterogeneous porous medium a number of times using a variable mixing time ($T_m$) between the two diffusion periods ($\Delta_1$) and ($\Delta_2$) to assess connectively between different regions in the medium. The d-PFG pulse sequence 300 can be used to correlate diffusion over the first diffusion period ($\Delta_1$) versus the second diffusion period ($\Delta_2$). A two-dimensional Laplace inversion can be used to analyze the obtained NMR signal data (E) using the following relationship:

$$E(q_1,q_2) = E(0,0)\exp(-D_1\Delta q_1^2 - D_2\Delta q_2^2) \tag{3}$$

where $D_1$ is the diffusion coefficient during the first diffusion period ($\Delta_1$) and $D_2$ is the diffusion coefficient during the second diffusion period ($\Delta_2$). This method of varying mixing times ($T_m$) does not measure or consider the time-dependent diffusion in porous media. The method uses a very long mixing times ($T_m$) to obtain a valid result, which in turn is problematic because the signal produced by the initial pair of gradient pulses decays over long mixing times. When a d-PFG pulse sequence 300 is used with a short mixing time ($T_m$), there is not sufficient movement of nuclei between the two different regions of the porous media. Thus, when the mixing time ($T_m$) is short, the diffusion coefficient during the first diffusion period ($\Delta_1$) and the diffusion coefficient during the second diffusion period ($\Delta_2$) are approximately equal.

For the reasons stated above, past diffusion measurements have difficulty effectively and efficiently differentiating between intrinsic bulk diffusivity of a fluid within a porous medium and the reduced diffusivity of the fluid caused by restricted diffusion.

SUMMARY

Illustrative examples of the present disclosure are directed to a method for determining a property of a substance using nuclear magnetic resonance (NMR). The method includes applying a NMR pulse sequence to the substance. The NMR pulse sequence includes a first set of pulses and a second set of pulses that encode for overlapping diffusion times. In some examples, one or more of the sets of pules is or includes a gradient waveform. A NMR signal produced by the NMR pulse sequence is detected to obtain NMR signal data. The property of the substance can be determined using the NMR signal data over each of the overlapping diffusion times. By overlapping diffusion times, the NMR pulse sequence can be used to measure a diffusion coefficient for a first diffusion time, a diffusion coefficient for a second diffusion time and a correlation between the overlapping diffusion times. This information, in turn, can be used to differentiate between intrinsic bulk diffusivity of the substance and the reduced diffusivity of the substance caused by restricted diffusion.

In accordance with some example implementations, a method includes applying a nuclear magnetic resonance (NMR) pulse sequence comprising a first set of pulses and a second set of pulses to a substance, wherein the first set of pulses encode for a first diffusion time and the second set of pulses encode for a second diffusion time, the first diffusion time overlapping the second diffusion time. The method also includes detecting a NMR signal produced by the NMR pulse sequence to obtain NMR signal data and applying to the substance a modified NMR pulse sequence generated by changing at least one of (a) the first diffusion time and (b) the second diffusion time. The method also includes detecting a NMR signal produced by the modified NMR pulse sequence to obtain NMR signal data, and determining a property of the substance using at least the NMR signal data over each of the overlapping diffusion times for the NMR pulse sequence and the modified NMR pulse sequence.

In accordance with some examples, a method includes generating decoupled gradient waveforms (distinct encoding modes), applying a nuclear magnetic resonance (NMR)

pulse sequence that includes the decoupled gradient waveforms to a substance, and detecting a NMR signal produced by the NMR pulse sequence to obtain NMR signal data. The method further includes determining a property of the substance based on the NMR signal data.

In some examples, A system for determining a property of a substance includes a nuclear magnetic resonance (NMR) system for applying NMR pulse sequences to a substance and detecting NMR signals generated by the substance to obtain NMR signal data, a processor, and a memory storing instructions. The instructions are executable by the processor to perform processes that include providing an NMR pulse sequence to the NMR system, the NMR pulse sequence including at least a first set of pulses and a second set of pulses, where the first set of pulses encode for a first diffusion time and the second set of pulses encode for a second diffusion time, the first diffusion time overlapping the second diffusion time. The processes further include determining a correlation in the NMR signal data with respect to diffusional motion of the substance during the first and second diffusion times encoded with respect to the first and second sets of pulses (e.g., gradient waveforms and/or other pulses); and determining the property of the substance using the NMR signal data over each of the overlapping diffusion times.

In other examples, the first set of pulses includes two pulses that are each defined by a first area parameter and separated by a time period. Similarly, the second set of pulses includes two pulses that are each defined by a second area parameter and separated by the time period. The NMR pulse sequence is applied a number of times and each application of the NMR pulse sequence uses different values for the first area parameter and/or the second area parameter. The method further includes detecting NMR signals produced by each application of the NMR pulse sequence to obtain NMR signal data. A Laplace inversion is performed on the NMR signal data to obtain diffusion coefficients for the first diffusion time and the second diffusion time. A property of the substance can be determined using these diffusion coefficients, such as a bulk diffusion coefficient of the substance.

In further examples, the first set of pulses and the second set of pulses include a portion of pulses that correspond to the first diffusion time and a complimentary portion of pulses that correspond to the second diffusion time. The values of the first area parameter and the second area parameter are varied according to the following relationships:

$$q_s = q_1 + q_2,$$

$$q_d = q_2 - q_1,$$

where $q_1$ is the first area parameter, $q_2$ is the second area parameter, $q_s$ is an area parameter for the portion of pulses that correspond to the first diffusion time, and $q_d$ is an area parameter for the complimentary portion of pulses that correspond to the second diffusion time.

Illustrative embodiments are also directed to a system for determining a property of a substance. The system includes an NMR system for applying NMR pulse sequences to a substance and detecting NMR signals generated by the substance to obtain NMR signal data. The system further includes a processor and a memory storing instructions executable by the processor to perform processes. Those processes include providing an NMR pulse sequence to the NMR system. The NMR pulse sequence includes a first set of pulses and a second set of pulses that encode for overlapping diffusion times. Furthermore, the processes include determining the property of the substance using the NMR signal data over each of the overlapping encoding times.

BRIEF DESCRIPTION OF THE DRAWINGS

Those skilled in the art should more fully appreciate advantages of various embodiments of the disclosure from the following "Description of Illustrative Embodiments," discussed with reference to the drawings summarized immediately below.

FIG. 28 shows odd/even symmetry about the same center point.

FIG. 29A shows $q_s/q_d$ pulses having the symmetry relation.

FIG. 29B shows variations on pulse shape and width.

FIG. 29C shows varying mixing times for $q_s$ and $q_d$.

FIG. 29D shows varying encoding times.

FIG. 29E shows correlation of vastly different diffusion times.

FIG. 30A shows oscillating gradients meeting the odd/even symmetry criteria.

FIG. 30B shows pertubations in the frequency of an oscillating gradient of FIG. 30A.

FIG. 30C shows perturbations in the number of oscillations of an oscillating gradient of FIG. 30A and meeting the odd/even symmetry criteria.

FIG. 30D shows the oscillating gradient pulses of FIG. 30A paired to make odd/even gradient waveforms in order to decouple oscillating gradient techniques.

FIGS. 31A to 31C show the odd/even symmetry property used to decouple different types of diffusion encoding gradients.

DETAILED DESCRIPTION

Illustrative examples of the present disclosure are directed to methods and systems for determining a property of a substance using nuclear magnetic resonance (NMR). The methods may includes applying an NMR pulse sequence to the substance.

In some examples, the pulse sequence includes a first set of pulses and a second set of pulses (e.g., first and second gradient waveforms and/or other pulses). The first set of pulses and the second set of pulses may encode for a first diffusion time and a second diffusion time. These diffusion times overlap. By overlapping diffusion times, the NMR pulse sequence can be used to measure a diffusion coefficient for the first diffusion time, a diffusion coefficient for the second diffusion time, and a correlation between the overlapping diffusion times. This information, in turn, can be used to differentiate between intrinsic bulk diffusivity of the substance and the reduced diffusivity of the substance caused by restricted diffusion. Details of various embodiments are discussed below.

In some examples, the pulse sequence includes pulses of a waveform. In some examples the pulse sequence includes rectangular pulses. In some examples, the pulse sequence includes a combination of rectangular pulses and waveform pulses.

Figure 1:
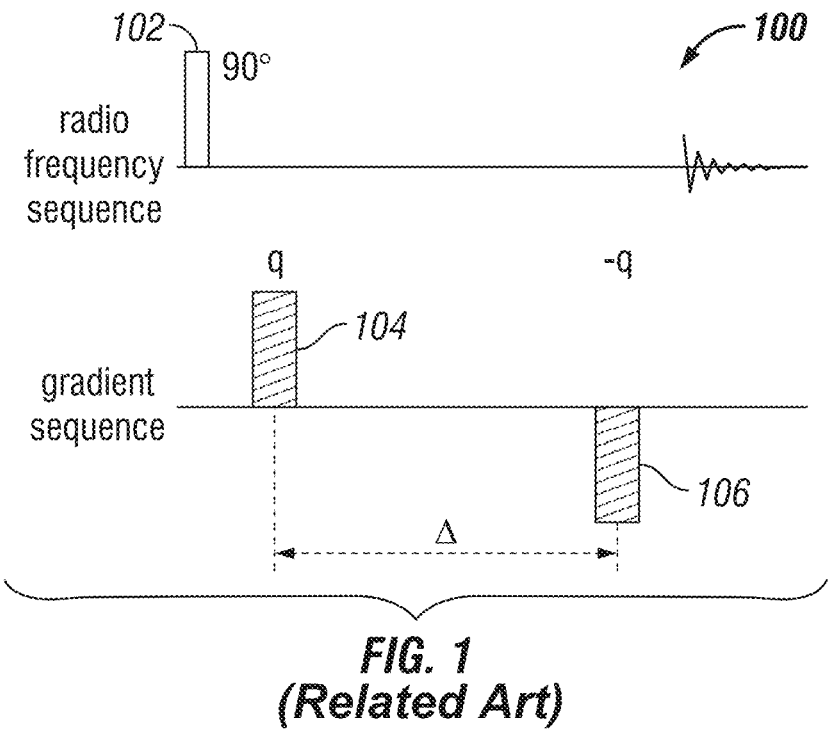
FIG. 1 shows a related art pulsed field gradient (PFG) sequence.
Figure 2:
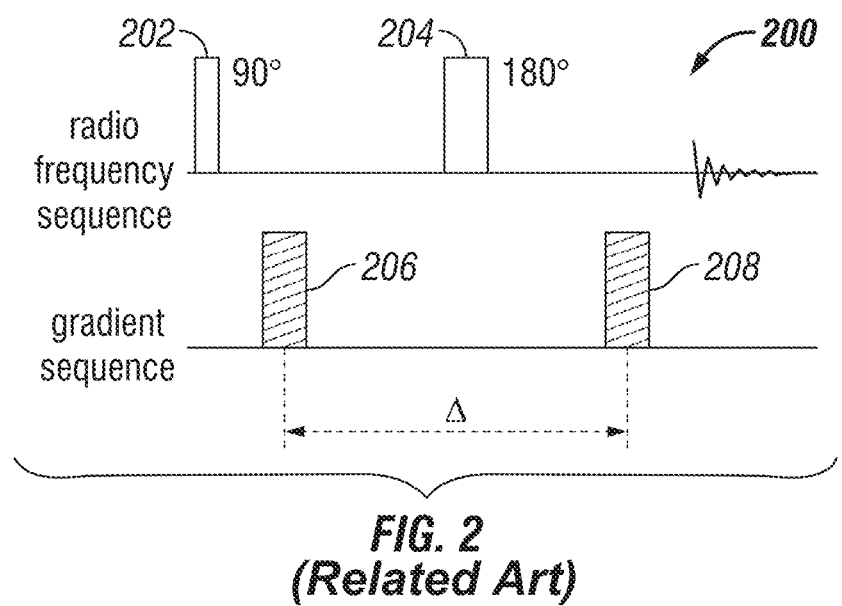
FIG. 2 shows another related art PFG sequence.
Figure 3:
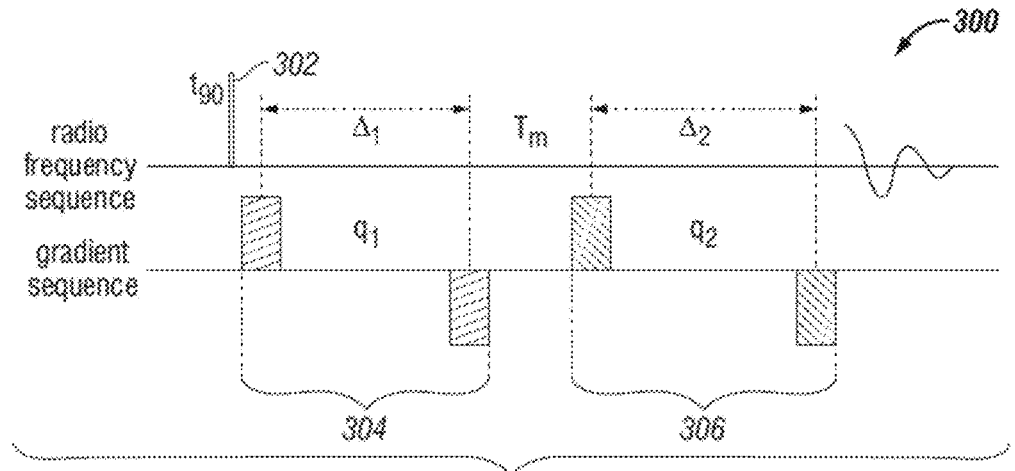
FIG. 3 shows a related art double-pulsed-field-gradient (d-PFG) sequence.
Figure 4:
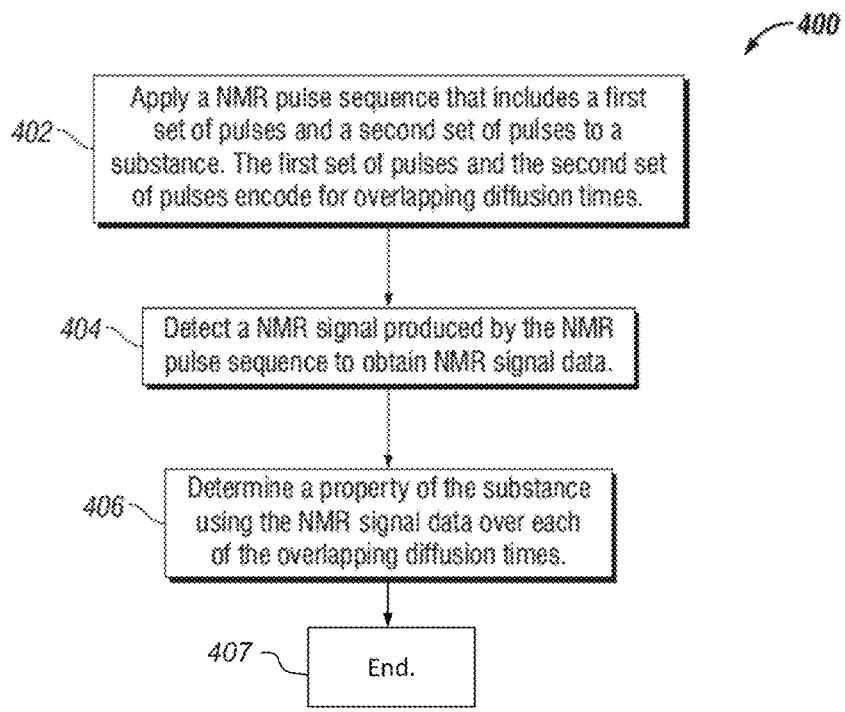
FIG. 4 shows a method for determining a property of a substance.
Figure 5:
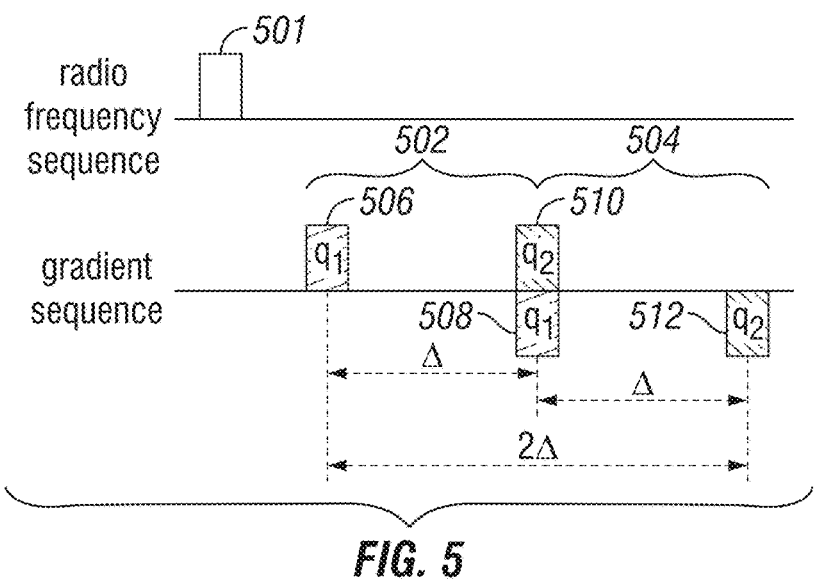
FIG. 5 shows a nuclear magnetic resonance (NMR) pulse sequence.

FIG. 4 shows a method 400 for determining a property of a substance using NMR. Before the first process 402, a sample, such as a rock core, is placed in an NMR system, such as an NMR rock core analyzer. Process 402 includes using the NMR system to apply a NMR pulse sequence to the substance. FIG. 5 shows one example of an NMR pulse sequence 500 that is applied to the substance. The NMR pulse sequence 500 includes a radio frequency excitation pulse 501 followed by at least a first set of pulses 502 and a second set of pulses 504. The first set of pulses 502 and the second set of pulses 504 are gradient pulses that generate a pulsed field gradient. A pulsed field gradient is a short, timed pulse with spatially dependent magnetic field intensity. In other embodiments, the first set of pulses 502 and the second set of pulses 504 are radio frequency pulses that are used to generate an "effective" pulsed field gradient, as further described below with respect to FIGS. 17 and 18. The sets of pulses may include one or more pulses. In this case, the first set of pulses 502 includes a first pulse 506 and a second pulse 508 that are each defined by a first area parameter ($q_1$) and separated by a time period ($\Delta$). The second set of pulses 504 includes a first pulse 510 and a second pulse 512 that are each defined by a second area parameter ($q_2$) and separated by the time period ($\Delta$). The area parameters are defined in units of reciprocal distance (e.g., mm$^{-1}$) and are defined by a pulse width ($\delta$) and a pulse height (g), as shown in equation 1. The first pulse 506, 510 and the second pulse 508, 512 within each set include area parameters that cancel. To this end, in some embodiments, the pulses have opposite amplitudes, as shown in FIG. 5.

The first set of pulses 502 and the second set of pulses 504 encode for overlapping diffusion times. In this case, the first set of pulses 502 and the second set of pulses 504 encode for a first diffusion time ($2\Delta$) and a second diffusion time ($\Delta$). As shown in FIG. 5, the diffusion times overlap because at least part of the second diffusion time ($\Delta$) is within the boundaries of the first diffusion time ($2\Delta$). The first set of pulses 502 and the second set of pulses 504 are applied consecutively to generate the overlapping diffusion times. More specifically, to generate the overlapping diffusion times, the first pulse 510 of the second set of pulses 504 is applied (i) simultaneously with the last pulse 508 of the first set 502, (ii) as soon as the last pulse ends, or (iii) a short time period after the last pulse ends. The short time period is short enough so that the magnetizations produced by each of the first set of pulses 502 ($q_1$) and the second set of pulses 504 ($q_2$) interact with each other to form overlapping diffusion periods. Furthermore, this short time period is short enough so that negligible diffusive motion occurs during the short time period relative to the diffusion times $\Delta$ and $2\Delta$. The short time period will be less than a shortest encoded diffusion time (e.g., the second diffusion time (Δ)) and, in various embodiments, will be less than five times the pulse width (δ) of the pulses within the two sets to optimally preserve the overlapping diffusion times.

In some embodiments, the NMR pulse sequence 500 may include more than two sets of pulses that encode for more than two diffusion times.

Figure 6:
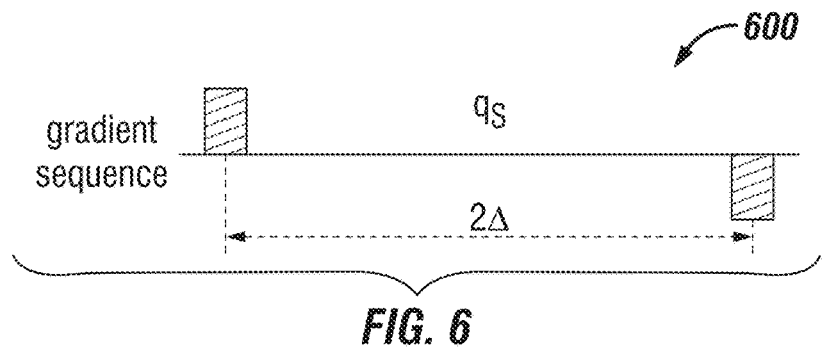
FIG. 6 shows a portion of pulses from the sequence in FIG. 5 that encode for a first diffusion time ($2\Delta$)
Figure 7:
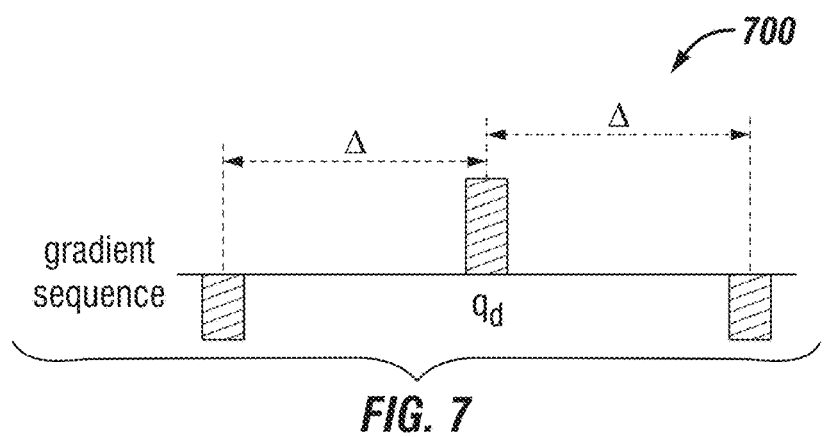
FIG. 7 shows a complimentary portion of pulses from the sequence in FIG. 5 that encode for a second diffusion time ($\Delta$)

The first set of pulses 502 and the second set of pulses 504 include a portion of pulses that correspond to the first diffusion time (2Δ) and a complimentary portion of pulses that correspond to the second diffusion time (Δ). FIG. 6 shows the portion of pulses 600 that are responsible for encoding the first diffusion time (2Δ). This portion of pulses 600 has an area parameter ($q_s$). FIG. 7 shows the complimentary portion of pulses 700 that is responsible for encoding the first diffusion time (2Δ) and also the second diffusion time (Δ). The complimentary portion of pulses 700 has an area parameter ($q_d$). The pulses 600, 700 shown in FIGS. 6 and 7 are portions of the first and second sets of pulses 502 ($q_1$) and 504 ($q_2$) in anti-symmetric ($q_s$) and symmetric ($q_d$) gradient waveforms. The area parameters for the portions 600, 700 are defined according to the following relationships:

$$q_s = q_1 + q_2, \quad (4)$$

$$q_d = q_2 - q_1, \quad (5)$$

where $q_1$ is the first area parameter, $q_2$ is the second area parameter, $q_s$ is the area parameter for the portion of pulses 600 that correspond to the first diffusion time (2Δ), and $q_d$ is the area parameter for the complimentary portion of pulses 700 that correspond to the second diffusion time (Δ).

Figure 8:
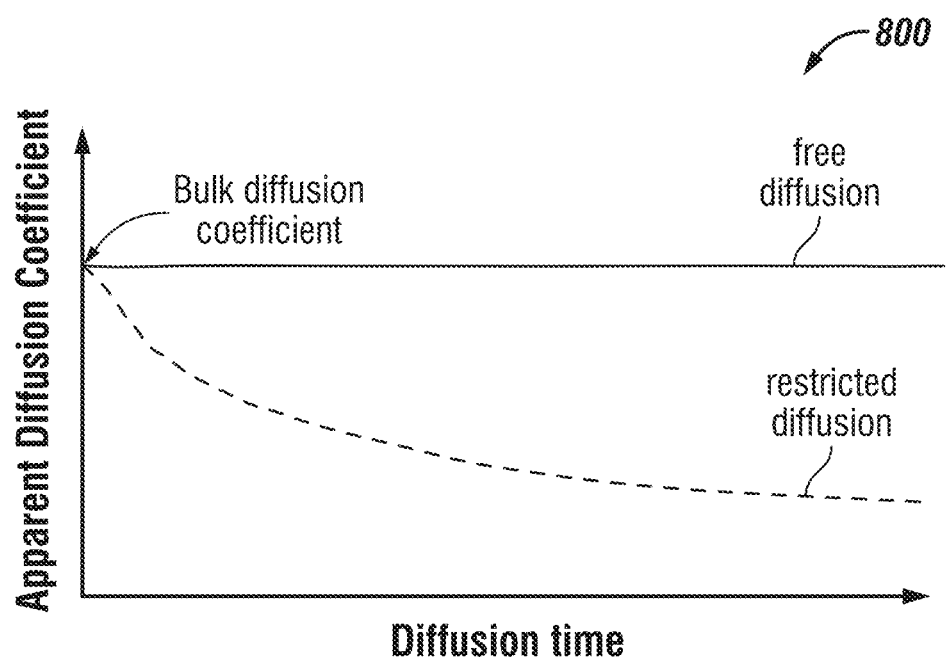
FIG. 8 shows a plot of diffusion coefficients versus diffusion time.

FIG. 8 shows a plot 800 for a diffusion coefficient versus diffusion time. As shown in the plot 800, when nuclei experience free diffusion (e.g., in an open environment), the diffusion coefficient is independent of the diffusion time and equivalent to the bulk diffusion coefficient. When nuclei experience restricted diffusion (e.g., in a porous medium), the diffusion coefficient varies with diffusion time. By encoding for two different diffusion times, the pulse sequences described herein can differentiate between restricted diffusion and bulk diffusion.

Figure 9:
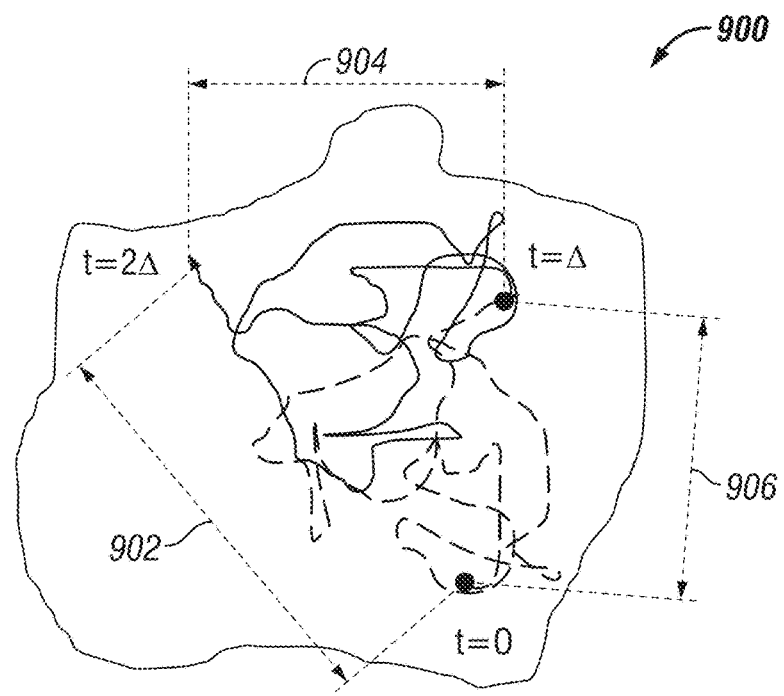
FIG. 9 shows a diffusion path for a nucleus over two different diffusion times that overlap.
Figure 10:
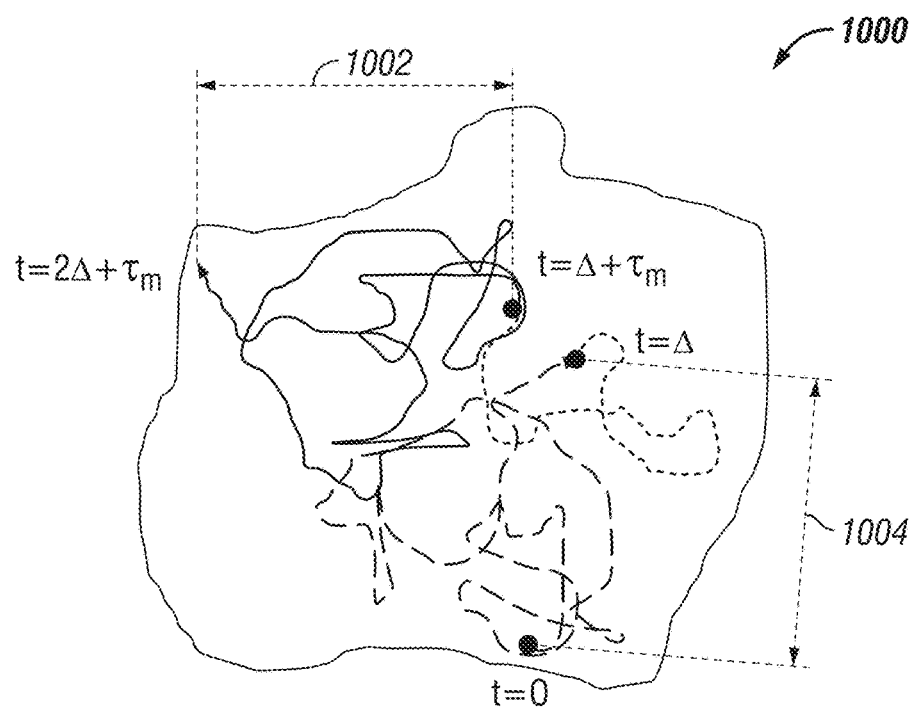
FIG. 10 shows a diffusion path for a nucleus over different diffusion times that do not overlap.

FIG. 9 shows a diffusion path 900 for a nucleus over two different diffusion times that overlap. Specifically, FIG. 9 shows how the portion of pulses ($q_s$) and complimentary portion of pulses ($q_d$) are sensitive to the movement of the nucleus over two different diffusion times. As shown in FIG. 9, the portion ($q_s$) is sensitive to displacement in directions 902 over the first diffusion time 2Δ. The complimentary portion of pulses ($q_d$) is sensitive to three displacements 902, 904 and 906 over the second diffusion time period (Δ). Because the portion ($q_s$) and the complimentary portion ($q_d$) are applied over overlapping diffusion times, the portions encode for the movement of the nucleus simultaneously and encode for diffusion over both the first diffusion time (2Δ) and the second diffusion time (Δ). Thus, an observation of diffusion over the second diffusion time period (Δ) can be correlated to its corresponding values for diffusion over the first time period (2Δ). In contrast, FIG. 10 shows a diffusion path 1000 over a first diffusion time and a second diffusion time that do not overlap (e.g., in the case of past d-PFG pulse sequences). In particular, FIG. 10 shows how a first set of pulses ($q_1$) and second set of pulses ($q_2$) are sensitive to the movement of the nucleus. The first set of pulses ($q_1$) is sensitive to displacement 1002 of the nucleus during the first diffusion time ($Δ_1$) and the second set of pulses ($q_2$) is sensitive to displacement in direction 1004 during the second diffusion time period ($Δ_2$). In this case, the diffusion times do not overlap and thus the pulse sequences are not sensitive to total displacement 902, as shown in FIG. 9. In the case of past d-PFG pulse sequences, when the first diffusion time ($Δ_1$) is equal to the second diffusion time ($Δ_2$), the pulse sequence and corresponding measurement are sensitive to diffusion over one time and, thus, cannot differentiate restricted diffusion from a reduction in the diffusion coefficient due to encoding time. When the first diffusion time ($Δ_1$) is different from the second diffusion time ($Δ_2$), the pulse sequence and corresponding measurement measure diffusion over two diffusion times, but the corresponding measurement cannot differentiate between restricted diffusion and nuclei exchange between two different environments, such as movement between two pores of different sizes. This is because displacements 1002 and 1004 are disjointed and may traverse two different environments. In contrast, the overlapping diffusion periods correspond to total displacement 902 using $q_s$ and its subdivisions 904, 906 using $q_d$.

Figure 11:
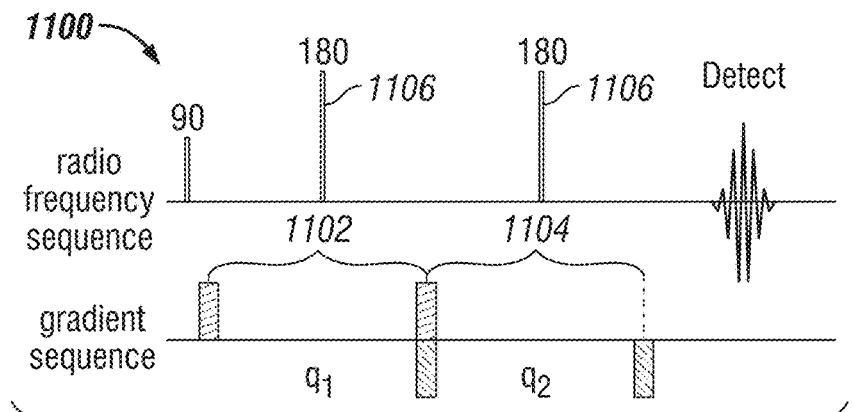
FIG. 11 shows a pulse sequence with refocusing pulses.

Illustrative embodiments of the present disclosure are not limited to the pulse sequence shown in FIG. 5. Other pulse sequences and additional pulse sequences can also be used to encode overlapping diffusion times. For example, FIG. 11 shows a pulse sequence 1100 with two sets of gradient pulses 1102, 1104 and refocusing pulses 1106 that minimize effects of background gradients. The refocusing pulses 1106 are 180 degree pulses that reverse the phase of spins produced by an excitation pulse and compensate for a range of different resonant NMR frequencies due to, for example, the use of an imperfect magnet. In various embodiments, the amplitudes of some of the gradient pulses are flipped to account for the effect of the RF pulses on the gradient encoding. For example, a 180 refocusing pulse will change the encoding done by a prior gradient pulse as if the gradient pulse were originally applied with the opposite sign. Thus, any subsequent gradient pulses account for that effective sign of the gradient pulse.

Figure 12:
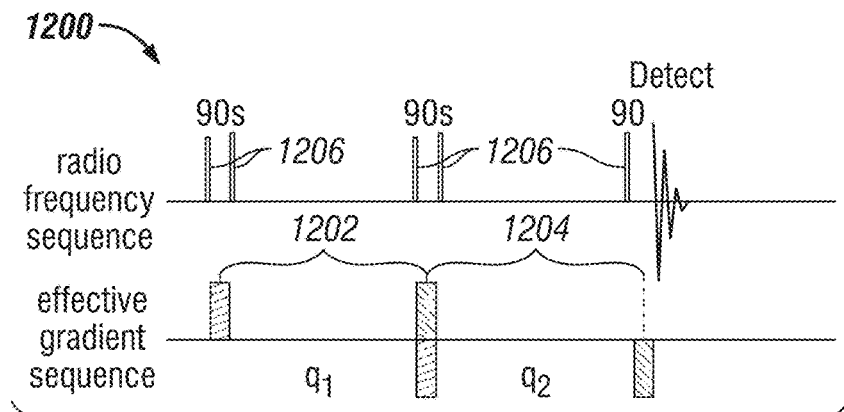
FIG. 12 shows a stimulated echo pulse sequence.

FIG. 12 shows a stimulated echo pulse sequence 1200 with two sets of gradient pulses 1202, 1204. 90-degree pulses 1206 store and re-excite spins from their longitudinal axes during encoding times. This pulse sequence minimizes signal decay and is generally used to increase the range of practical encoding times.

Figure 13:
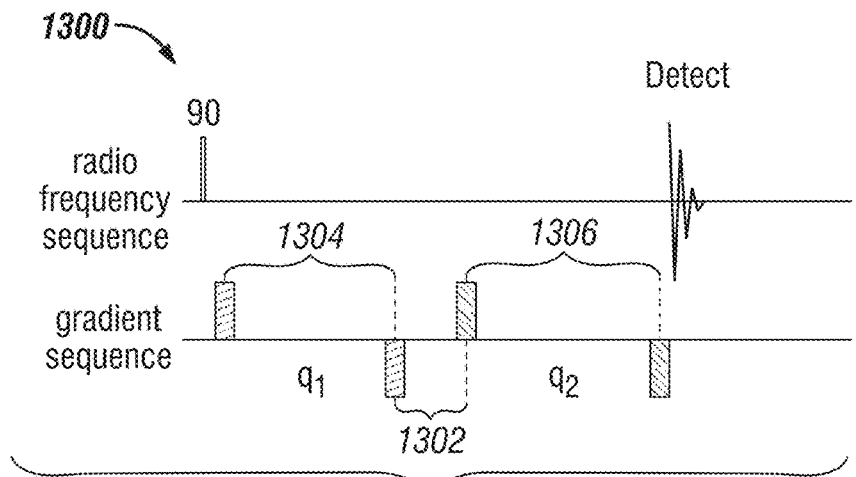
FIG. 13 shows a pulse sequence with a short time period between the two sets of pulses.

FIG. 13 shows a pulse sequence 1300 with a short time period 1302 between the two sets of pulses 1302, 1306.

Figure 14:
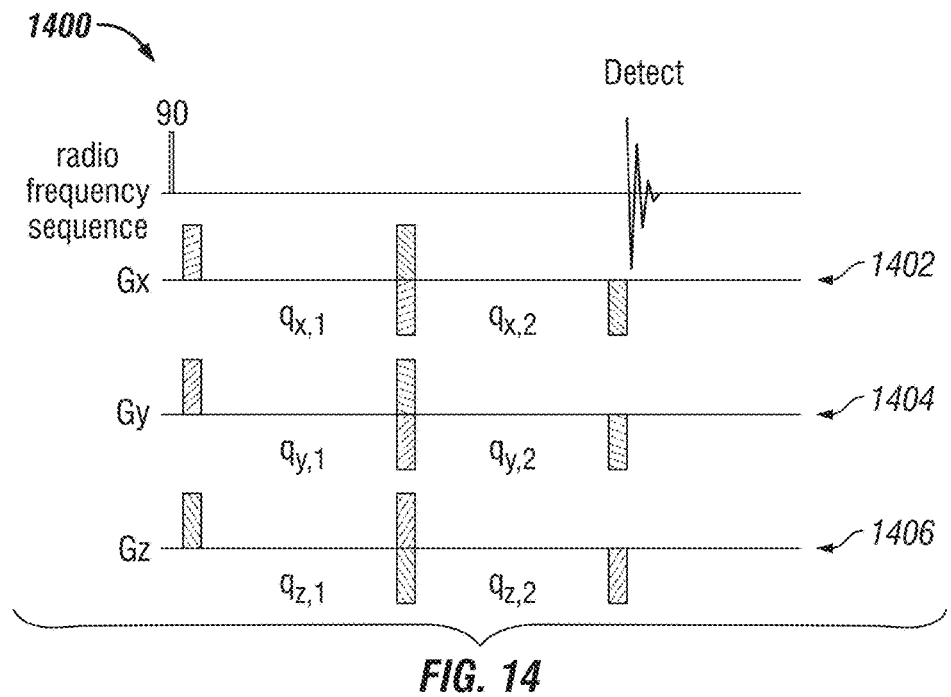
FIG. 14 shows a pulse sequence with multiple gradient axes pulses.

FIG. 14 shows a pulse sequence 1400 with multiple gradient axes pulses. Often pulse field gradient encoding is done with gradients along different spatial axes. In this case, the pulse sequence 1400 includes an excitation pulse followed by two sets of gradient pulses in the x-direction 1402, y-direction 1404 and z-direction 1406.

Figure 15:
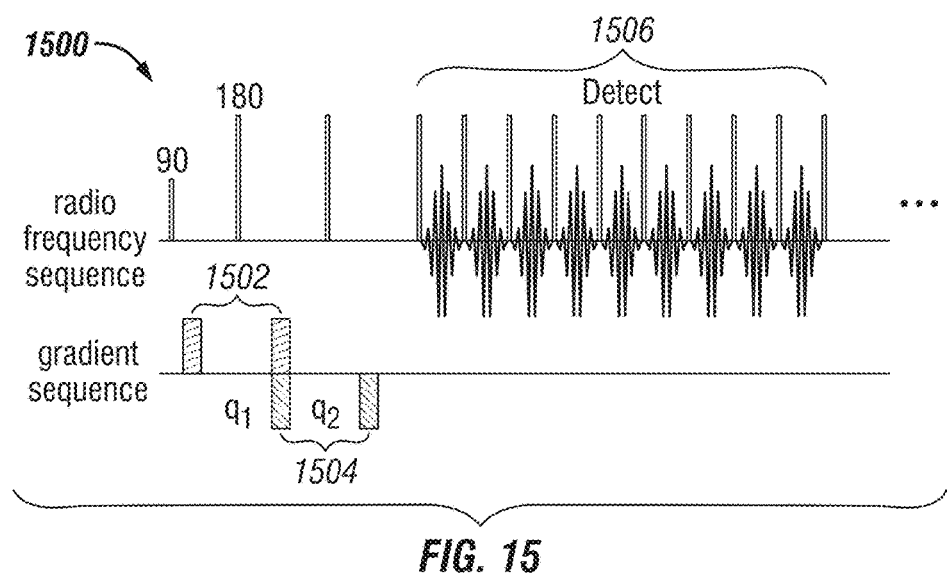
FIG. 15 shows a pulse sequence with a Carr Purcell Meiboom Gill (CPMG) encoding/detection.

FIG. 15 shows a pulse sequence 1500 with an additional encoding. The two sets of gradient pulses described herein can precede or follow any other type of NMR encoding (e.g., relaxation encoding, or imaging encoding). In this example, the two sets of gradient pulses 1502, 1504 are followed by a Carr Purcell Meiboom Gill (CPMG) acquisition 1506 to encode for $T_2$ relaxation.

Referring back to FIG. 4, at process 404, a NMR signal produced by the NMR pulse sequence within the substance is detected to obtain NMR signal data over the first and second diffusion time periods. In some embodiments, at process 406, the method ends at 407 once the NMR signal data over each of the overlapping diffusion times is then used to determine a diffusion coefficient of the substance. For example, if the diffusion coefficient at the first diffusion time (2Δ) is equal to the diffusion time at the second diffusion time (Δ), then the measured diffusion coefficient can be assumed to be the bulk diffusion coefficient.

In various other embodiments, processes 402 and 404 are repeated so that the NMR pulse sequence is applied to the substance a plurality of times using different values of area parameters for the portion of pulses ($q_s$) and the complimentary portion of pulses ($q_d$). The area parameters for the portions ($q_s$) and ($q_d$) can be varied by modifying the area parameters for the first and second sets of pulses ($q_1$) and ($q_2$) according to the relationships in equations 4 and 5. After each pulse sequence is applied, the generated NMR signal is detected to obtain an array of NMR signal data ordered according to $q_s$ and $q_d$ coordinates. In other embodiments, however, the area parameters for the first and second sets of pulses ($q_1$) and ($q_2$) are not varied according to the relationships in equations 4 and 5. Instead, each of the area parameters for the first and second sets of pulses ($q_1$) and ($q_2$) is varied to obtain an array of NMR signal data ordered according to, for example, $q_1$ and $q_2$ coordinates At process 406, the NMR signal data obtained from the repetitive application of the NMR pulse sequence to the substance is then used to determine a property of the substance. In particular, NMR signal data over each of the overlapping diffusion times is used to determine the property of the substance. The NMR signal produced by the NMR pulse sequence can be approximated by the following relationship:

$$\text{Ln } [E(q_1,q_2)] = -\Delta[q_1^2 D(\Delta) + q_2^2 D(\Delta) + 2q_1(D(2\Delta) - D(\Delta))q_2] \quad (6)$$

Equation 6 was derived by using an approximation of a d-PFG signal, such as the approximation described in Sune Norhoj Jespersen, Equivalence of Double and Single Wave Diffusion Contrast at Low Diffusion Weighting, NMR in Biomedicine (Dec. 2, 2011). The approximation also assumed zero mixing time ($T_m=0$) and identical encoding times ($\Delta=\Delta_1=\Delta_2$). Accordingly, the generated NMR signal reflects the time dependence of diffusion over the times Δ and 2Δ. Using the variables established in equations 4 and 5, the signal equation above for d-PFG with zero mixing time can be written as the following relationship:

$$E(q_s, q_d) = \exp\left\{-\frac{1}{2}\Delta[q_s^2 D(2\Delta) + q_d^2(2D(\Delta) - D(2\Delta))]\right\} \quad (7)$$

In the framework of $q_s$ and $q_d$, the contribution from $q_s$ and $q_d$ are separated and there are no cross-terms between $q_s$ and $q_d$. The two terms independently encode for diffusion over different and overlapping times—$D(2\Delta)$ for $q_s$ and $2D(\Delta)-D(2\Delta)$ for $q_d$. "$D(2\Delta)$" and "$2D(\Delta)-D(2\Delta)$" are referred to herein as $D_s$ and $D_d$, respectively. In various embodiments, the second diffusion coefficient $D_d$ can be approximated as $D(\Delta)$.

The relationship disclosed in equation 7 can be used to analyze NMR signal data in order to determine a property of the substance, such as presence of restricted diffusion, by observing a difference in $D(2\Delta)$ and $D(\Delta)$ in the fit of equations 7 to the NMR signal data. In additional or other embodiments, a Laplace inversion is applied to the NMR signal data, as described below. The relationship defined by Equation 7 is different from the relationship defined by equation 6. The relationship defined by equation 6 exhibits a direct cross-term between $q_1$ and $q_2$. As a result, the relationship in equation 2 produces an incorrect result when the mixing time ($T_1$) of the d-PFG pulse is short. The new approach defined by equation 7 takes into consideration the relationship due to time-dependent diffusion and removes the cross-term.

For substances that contain a range of diffusion coefficients due to material mixture or pore size distribution, the relationship below can be used to approximate the NMR signal:

$$E(q_s, q_d) = \int dD f(D_s, D_d) \exp\left\{-\frac{1}{2}\Delta(q_s^2 D_s + q_d^2 D_d)\right\} \quad (8)$$

where $f(D_s, D_d)$ is a distribution function for diffusion coefficients that correspond to the number of nuclei whose diffusion coefficients at Δ and 2Δ correspond to ($D_s$, $D_d$). Equation 8 was derived by taking the integral of equation 7 over the distribution of diffusion coefficients. Accordingly, the NMR signal data obtained for independently selected values of $q_s$ and $q_d$ can be analyzed using equations 7 and 8 to obtain a two-dimensional plot of diffusion at the first diffusion time ($D_s$) versus diffusion at the second diffusion time ($D_d$).

Figure 16:
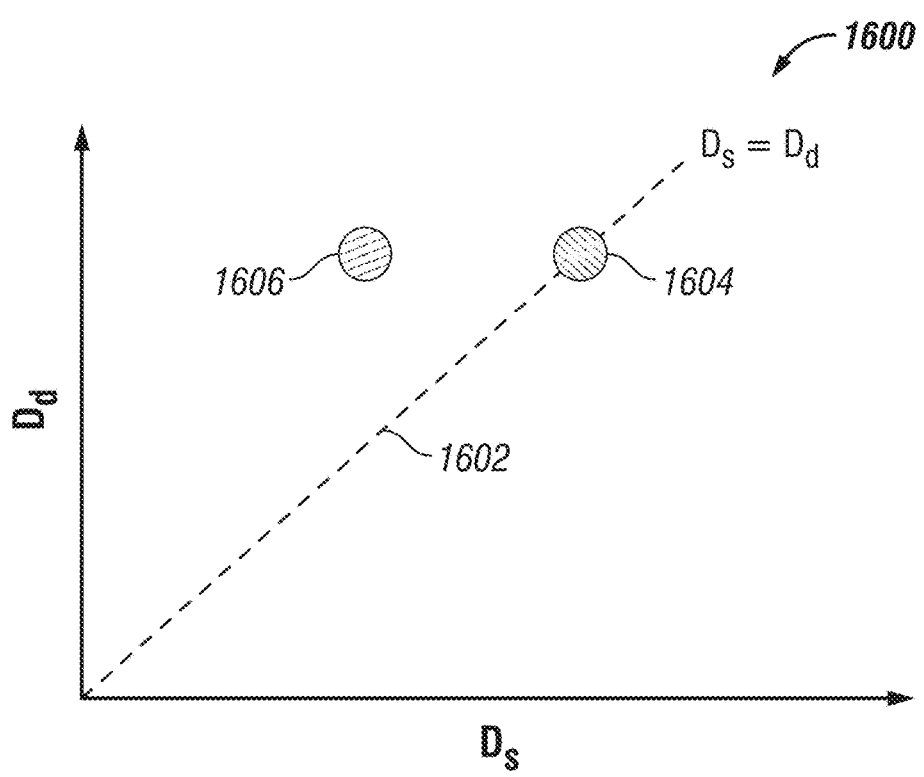
FIG. 16 shows a two-dimensional plot of diffusion coefficients at a first diffusion time ($D_S$) versus diffusion coefficients at the second diffusion time ($D_D$)

Given the array of NMR signal data ordered according to $q_s$ and $q_d$ coordinates. The two-dimensional plot is obtained by using a Laplace inversion and solving for $D_s$ and $D_d$ in equation 8. FIG. 16 shows a two-dimensional plot 1600 of diffusion coefficients at the first diffusion time ($D_s$) versus diffusion coefficients at the second diffusion time ($D_d$). For bulk diffusion, the diffusion coefficient is independent of the encoding time. Accordingly, the first diffusion coefficient ($D_s$) is equal to the second diffusion coefficient ($D_d$) and both are equal to the bulk diffusion coefficient ($D_0$). In this case, the NMR signal will appear on a diagonal line ("on-diagonal") 1602, as shown by component 1604 in FIG. 16. If the NMR signal or components of the NMR signal appear away from the diagonal line 1602 ("off-diagonal"), such as component 1606 in FIG. 16, then the first diffusion coefficient ($D_s$) and the second diffusion coefficient ($D_d$) are different. The off-diagonal components unambiguously identify the presence of restricted diffusion. Such variations in the time dependence of the apparent diffusion coefficient (D) is characteristic of restricted diffusion and will not occur due to fluid composition.

The off-diagonal components of the NMR signal can yield further information about the porous medium and fluid within the pore volumes of the porous medium. For example, the first coefficient ($D_s$) and the second diffusion coefficient ($D_d$) can be used to yield both pore size (e.g., a surface to volume ratio) and the bulk diffusion coefficient ($D_0$) of the fluid. The bulk diffusion coefficient (e.g., for fluid typing) and the pore size can be determined without knowing or assuming the specific fluid or pore size of the porous medium. For example, according to a short time diffusion approximation, restricted diffusion can be determined by the following relationship:

$$D_R(\Delta) \approx D_0\left[1 - \left(\frac{4}{9\sqrt{\pi}}\right)\left(\frac{S}{V}\right)\sqrt{D_0 \Delta}\right] \quad (9)$$

where $D_R(\Delta)$ is the restricted diffusion over a time period Δ, $D_0$ is the bulk diffusion coefficient, S is the surface area of the pores within the porous medium, and V is the volume of the pores within the porous medium. A short diffusion limit approximation can be applied in cases when addition information about the porous medium is not used (e.g., tortuosity or bulk diffusion coefficient). The short time diffusion approximation is derived in Mitra et al., Short-Time Behavior of the Diffusion Coefficient as a Geometrical Probe of Porous Media, Physical Review B, Vol. 47, No. 14, p. 8565-8574 (Apr. 1, 1993). The bulk diffusion coefficient can be determined according to the following relationship:

$$D_0 = \frac{\sqrt{2}\,D(\Delta) - D(2\Delta)}{\sqrt{2} - 1} \qquad (10)$$

where $D(2\Delta)$ is the first diffusion coefficient ($D_s$) and $D(\Delta)$) is the combination $(1/2)*(D_d+D_s)$ of the second and first diffusion coefficient. The surface to volume ratio can be determined according to the following relationship:

$$\frac{S}{V} = \frac{9}{4}\sqrt{\frac{(\sqrt{2}-1)\pi}{\Delta}}\,\frac{D(\Delta) - D(2\Delta)}{\left(\sqrt{2}\,D(\Delta) - D(2\Delta)\right)^{\frac{3}{2}}} \qquad (11)$$

Various other formulations for the time dependent diffusion coefficient can also be applied to interpret the two-dimensional plot of diffusion at the first diffusion time ($D_s$) versus diffusion at the second diffusion time ($D_d$). For example, the Pade approximation can be used to incorporate a long time diffusion approximation of the diffusion coefficient, which includes the effects of tortuosity.

Various embodiments of the present disclosure are also directed to selecting appropriate pulse sequence parameters (e.g., diffusion time ($\Delta$ and $2\Delta$)) to accurately determine the bulk diffusion coefficient and surface-to-volume ratio. In some cases, the NMR signal may be on-diagonal (within a certain error) even though the nuclei within the pore volumes experience restricted diffusion. This condition may happen when the ratio of (i) the distance the nuclei diffuse to (ii) the pore size is small. Pore size scales as the reciprocal of the surface to volume ratio. The diffusion distance to pore size ratio is defined by a dimensionless number, referred to as $l_r$, and the following relationship:

$$l_r = (S/V)\sqrt{D_0\Delta} \qquad (12)$$

Equation 12 and the dimensionless number characterizes a range of pore sizes that can be accurately investigated using particular diffusion times ($\Delta$ and $2\Delta$). By using equation 12, appropriate diffusion times can be selected for a particular pore size and fluid type. Otherwise, in some cases, the diffusion distance of the nuclei will be too short to detect significant restricted diffusion in large pores (e.g., small $l_r$). In another case, for a closed pore network, the diffusion distance of the nuclei will be too long (e.g., large $l_r$) for a small pore size and diffusion attenuation will not be significantly different between $\Delta$ and $2\Delta$. In yet another example, for an open pore network, the diffusion distance of the nuclei will be too long (e.g., large $l_r$) for a small pore size and diffusion attenuation will approach a tortuosity limit (e.g., where $D(\Delta)$ does not significantly change).

To ensure that a desired range of restriction sizes is observable, numerical limits on the diffusion distance to pore size ratio ($l_r$) can be determined in order to evaluate sequence parameters ($\Delta$) for a given fluid type ($D_0$) and target restriction size. When pores are too large then $l_r$ is small (e.g., $l_r$ is less than 1) and the measurement will be limited by its ability to resolve small changes in the diffusion coefficient. The following relationship can be used to evaluate the change between the measured time dependent diffusion coefficients $D_d$ and $D_s$ at small $l_r$ by calculating a ratio between $D_d$ and $D_s$.

$$\frac{D_d}{D_s} = 2\frac{1 - \kappa l_r}{1 - \sqrt{2\kappa l_r}} - 1, \kappa = \frac{4}{9\sqrt{\pi}}, \qquad (13)$$

Thus, given a minimum desired contrast between $D_d$ and $D_s$, a lower bound for $l_r$ can be determined. For example, a 1% change between $D_s$ and $D_s$ (a ratio of 1/0.99) corresponds to a diffusion distance to pore size ratio ($l_r$) that is greater than 0.046.

An upper bound for the diffusion distance to pore size ratio ($l_r$) can also be estimated. For the upper bound, there are two cases to consider. In a first case, the sample includes a closed pore network (e.g., plant cells). In a second case, the sample includes, an open pore network (e.g., a rock core). For a closed pore network, at long diffusion times ($\Delta$), the diffusion length will greatly exceed the pore size, but displacement of nuclei will be fixed by the pore size and, thus, the apparent diffusion coefficient will stop varying with diffusion time. An open pore network, at long diffusion times ($\Delta$), will act as a free diffusion environment, but the apparent diffusion coefficient will be reduced from the true bulk value, as explained in Latour et al., Time-Dependent Diffusion Coefficient of Fluids in Porous Media as a Probe of Surface-to-Volume Ratio, Journal of Magnetic Resonance, Series A, Vol. 101, Issue 3, p. 342-346 (Feb. 15, 1993). Thus, the apparent diffusion coefficient for the open pore network will also stop varying with diffusion time. The diffusion distance to pore size ratio ($l_r$) is selected so that the ratio is sufficiently small to avoid a point where the apparent diffusion coefficient will stop varying with diffusion time. In some embodiments, the diffusion distance to pore size ratio ($l_r$) is selected to be less than five (e.g., $l_r<5$). For example, for sandstone rocks with large grains, the point where the apparent diffusion coefficient will stop varying with diffusion time is typically not reached because the NMR signal will decay before reaching large values of diffusion time ($\Delta$). For carbonate rocks with fine grains, this point can be reached and thus the diffusion distance to pore size ratio ($l_r$) can be appropriately adjusted.

In various embodiments, the first set of pulses and the second set of pulses are pulsed field gradient pulses. For example, pulse sets 502 and 504 in FIG. 5 may be pulsed field gradient pulses. The pulsed field gradient pulses are applied to a substance using a gradient coil. In other embodiments, the pulse sets 502 and 504 can be radio frequency pulses that are applied to the substance using a constant field gradient produced by, for example, a permanent magnetic array. The radio frequency pulses in combination with the constant background gradient produce an "effective" pulsed field gradient within the substance. An effective pulsed field gradient has an equivalent effect on spin magnetization as a pulsed field gradient applied with a gradient coil.

Figure 17:
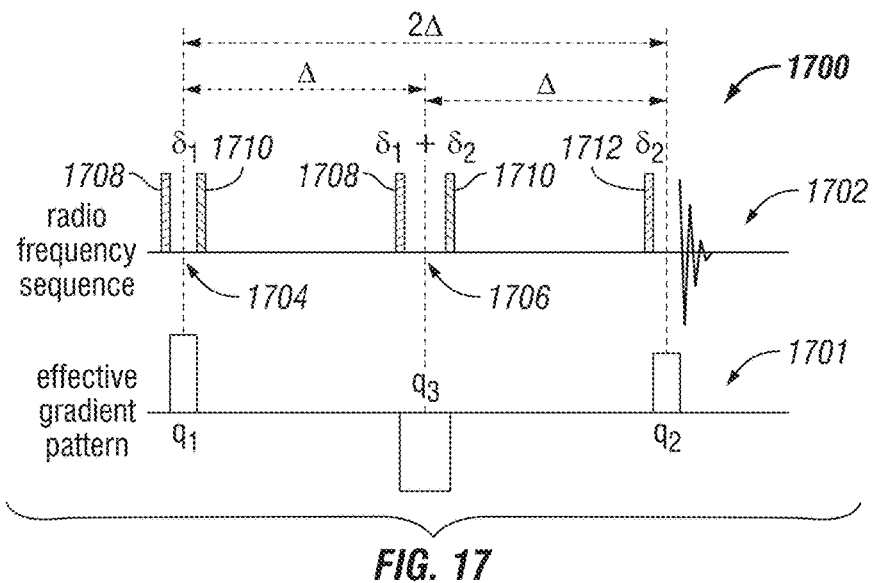
FIG. 17 shows an NMR pulse sequence that generates an effective pulsed field gradient using a constant background gradient.

The effective pulsed field gradient can be produced by using pairs of pulses that encode the effective pulsed field gradient. FIG. 17 shows an NMR pulse sequence 1700 that generates an effective pulsed field gradient pattern 1701. The pulse sequence 1700 includes a series 1702 of 90-degree radio frequency pulses. The series 1702 includes a first pair of pulses 1704 and a second pair of pulses 1706. The first pulse 1708 within each pair rotates a spin magnetization of the nuclei to a transverse plane and begins gradient encoding. The second pulse 1710 in each pair rotates the spin magnetization back to a longitudinal axis and ends the gradient encoding. As shown in FIG. 17, the series of pulses 1702 effectively produce a corresponding effective gradient pattern 1701. The second 90-degree pulse in the last pair of pulses 1712 is omitted so that the NMR signal produced by the sequence 1700 can be detected. In the example shown in FIG. 17, the area parameters $q_1$ and $q_2$ are defined by the following relationships:

$$q_1 = \gamma g \delta_1, \tag{14}$$

$$q_2 = \gamma g \delta_2 \tag{15}$$

where $\delta_1$ and $\delta_2$ are the time periods between the pulses, as shown in FIG. 17. Accordingly, encoding for $q_s$ and $q_d$, as described above, can be accomplished by selecting $\delta_1$ and $\delta_2$ appropriately.

Figure 18:
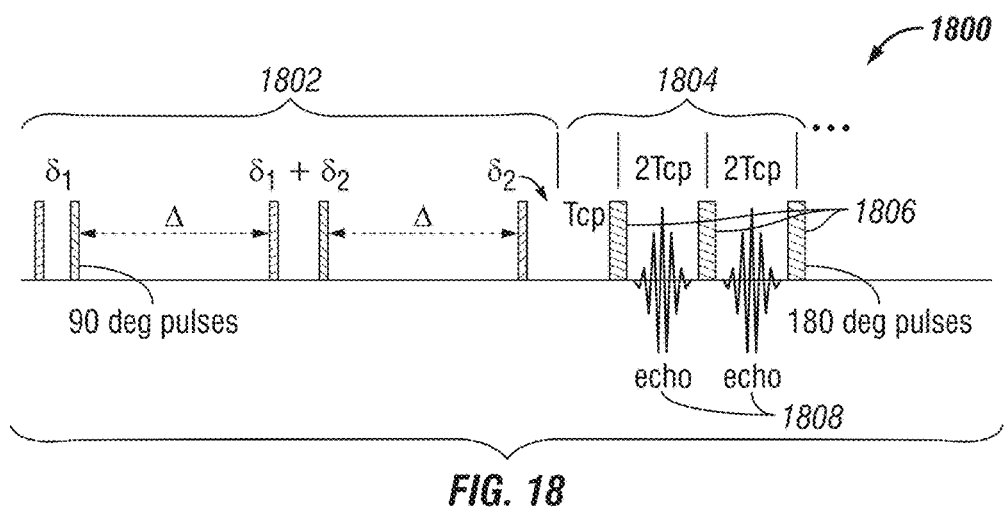
FIG. 18 shows an NMR pulse sequence that generates an effective pulsed field gradient.

A number of refocusing pulses (e.g., 180-degree pulses) can follow the series of pulses and can be used to obtain $T_2$ relaxation time for the NMR signal. FIG. 18 shows a NMR pulse sequence 1800 with a series of pulses 1802 that generate an effective pulsed field gradient pattern followed by a CPMG sequence 1804. As shown in the FIG. 18, a 180-degree refocusing pulse 1806 is applied after each signal echo 1808 with a detection echo time of $2T_{cp}$. The CPMG sequence 1804 is used to record the signal decay, in a similar manner to $T_1$-$T_2$ and D-$T_2$ correlation techniques are applied. Such pulse sequences can be used in conjunction with NMR logging tools that employ permanent magnet arrays and produce field gradients that are constant in time.

Figure 19:
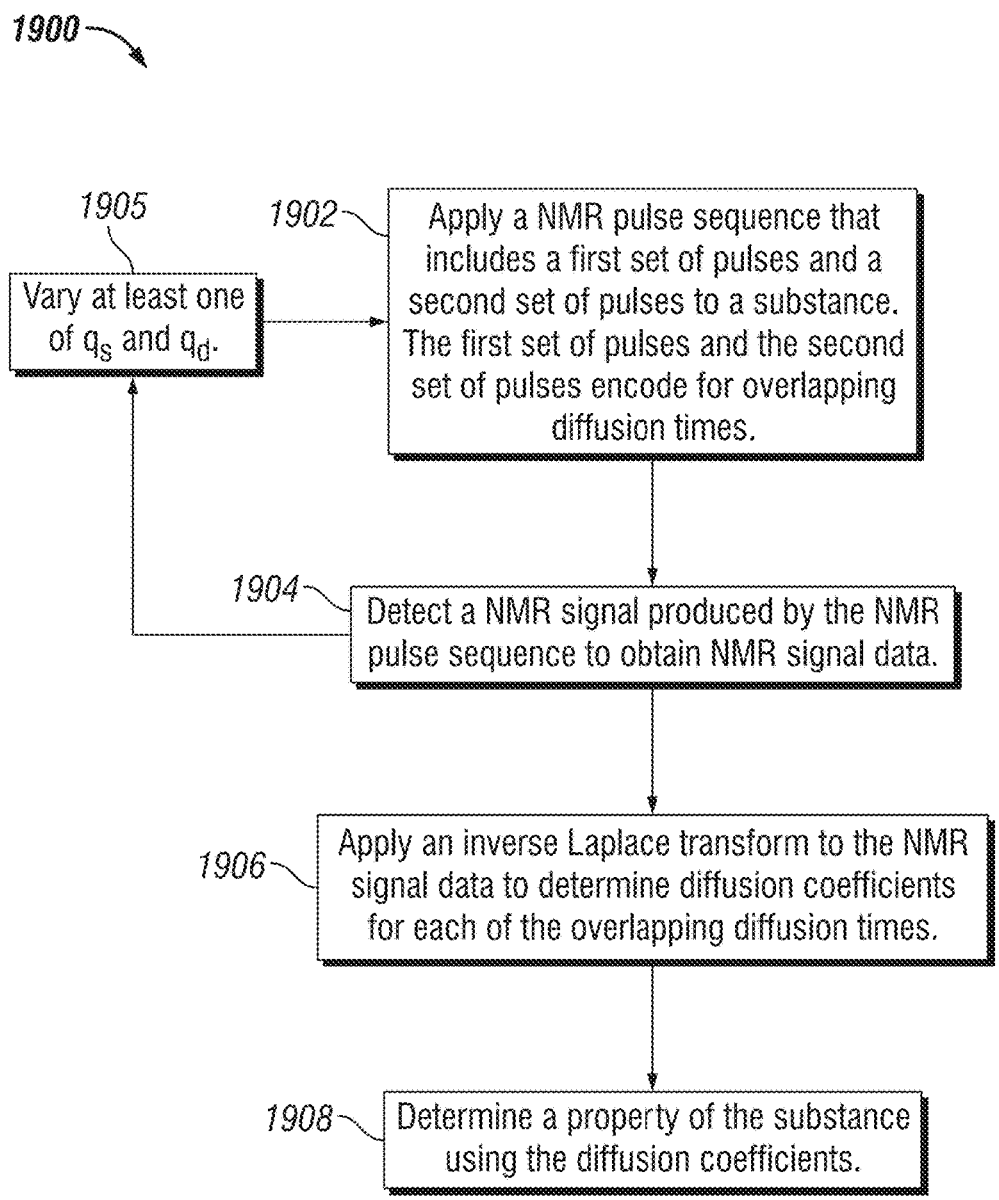
FIG. 19 shows a method for determining a property of a substance.

FIG. 19 shows another method 1900 for determining a property of a substance using NMR. Before the first process 1902, a sample is placed in an NMR system. The sample may be a rock core, a food sample or a biological tissue. The NMR system may be a NMR rock core analyzer, a clinical or animal MRI, a portable NMR device, or a high field NMR spectrometer used in, for example, chemical spectroscopy. Process 1902 includes using the NMR system to apply a NMR pulse sequence to the substance. As explained above, the NMR pulse sequence includes at least a first set of pulses and a second set of pulses that encode for overlapping diffusion times. In particular, the NMR pulse sequence encodes for a first diffusion time ($2\Delta$) and a second diffusion time ($\Delta$), such as the pulse sequence 500 shown in FIG. 5. These sets of pulses include "portions" that have area parameters referred to herein as $q_s$ and $q_d$, as described above. The NMR signal data produced by the NMR pulse sequence is detected at process 1904.

Processes 1902 and 1904 are repeated a number of times (e.g., one or more times) using different values of $q_s$ and $q_d$ to obtain an array of NMR signal data ordered according to $q_s$ and $q_d$ coordinates (1905). The values of $q_s$ and $q_d$ can be varied independently. For example, for each value of $q_s$, several values of $q_d$ can be used. And vice versa, for each value of $q_d$, several values of $q_d$ can be used. The values for $q_s$ and $q_d$ may be uniformly spaced, logarithmically spaced, or have some other non-uniform spacing. Also, in some embodiments, $q_s$ and $q_d$ are aligned along the same spatial orientation if the orientation is not varied (e.g., the sample may be anisotropic). The measurement may then be repeated for other orientations. In another embodiment, a full sampling of $q_s$ and $q_d$ of magnitude and orientation space (e.g., forming a grid in x,y,(z)) may be used to obtain a map for the directionality of the first diffusion coefficient ($D_s$) versus the second diffusion coefficient ($D_d$). As an example, the directionality of each of these terms can be approximated by a tensor of a type that is similar to the type used in diffusion tenor imaging (DTI), which is common in the medical MRI field. Other pulse sequences can also be used. For example, an inversion recovery for $T_1$ relaxation time can be added before the first set and second set of pulses. In another example, a CPMG sequence for determining $T_2$ relaxation time or an MRI imaging sequence can be added after the first and second sets of pulses.

Figure 20:
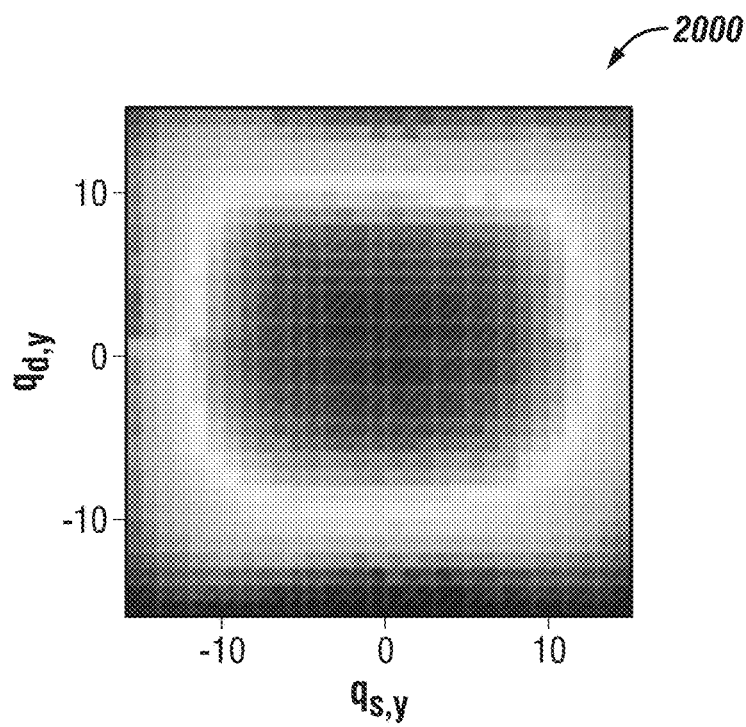
FIG. 20 shows an array of NMR signal data for a potato sample.
Figure 21:
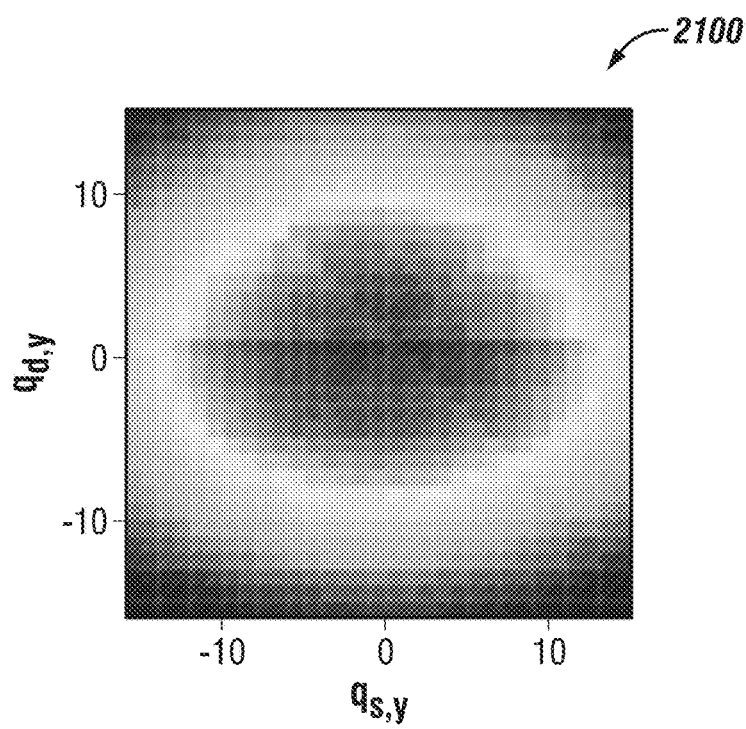
FIG. 21 shows an array of NMR signal data for an avocado sample.

In various embodiments, the array of NMR signal data can be used to determine properties of the sample. For example, a faster decay along the $q_d$ axis than the $q_s$ axis indicates restricted diffusion. FIG. 20 shows an array of NMR signal data for a potato sample 2000. As shown in FIG. 20, the potato sample exhibits a faster decay along the $q_d$ axis than the $q_s$ axis. Furthermore, a non-ellipsoidal shape, as shown in FIG. 20, indicates a wide range of restriction sizes. In comparison, FIG. 21 shows an elliptical decay for an avocado sample 2100. Different pore sizes will produce different $D(\Delta)/D(2\Delta)$ ratios and ellipsoids of varying eccentricity. In further embodiments, the array of NMR signal data is fit to a curve to determine effective $D(\Delta)$ to $D(2\Delta)$ scalar values for the sample by fitting a 2-dimensional Gaussian. If the orientations, in addition to the magnitudes, of $q_s$ and $q_d$ were varied, a full effective tensor approximation for $D(\Delta)$ and $D(2\Delta)$ can be determined by fitting a multi-dimensional Gaussian. In some embodiments, a fit up to the fourth order is made to include Kurtosis at the first diffusion time ($2\Delta$) and the second diffusion time ($\Delta$) in addition to Gaussian diffusion. Other decay shapes can also be used, such as a stretched exponential (e.g., $d_{\alpha,\beta}(t) = \exp\{-\alpha t^\beta\}$). Such decay shapes can be further tailored to fit $q_s$ and $q_d$. For example, given a one-dimensional stretched exponential $d_{\alpha,\beta}(|q|)$, a product $d_{s,\alpha,\beta}(|q_s|) \, d_{a,\alpha,\beta}(|q_d|)$ can be fit for $\alpha_s$, $\beta_s$, $\alpha_d$, $\beta_d$.

At process 1906, the method includes applying an inverse Laplace transform to the NMR signal data to obtain diffusion coefficients at each of the overlapping diffusion times. In particular, a two-dimensional inverse Laplace transform is applied to the array of NMR signal data along $q_s$ and $q_d$ to determine a two-dimensional plot of diffusion at the first diffusion time ($D_s$) versus diffusion at the second diffusion time ($D_d$), such as the one shown in FIG. 16. The two-dimensional inverse Laplace transform can be repeated for other spatial axis of $q_s$ and $q_d$ gradients. Furthermore, in some embodiments, additional encoding axes may also be inverted or fit. For example, with a CPMG acquisition, the $T_2$ relaxation time can be fit as a third dimension to an exponential decay or inverted for a third inverse Laplace dimension as a $T_2$ relaxation axis.

At process 1908, properties of the substance can be determined from the two-dimensional plot of diffusion coefficients at the first diffusion time ($D_s$) and diffusion coefficients at the second diffusion time ($D_d$). For example, the value of $D_s$ and $D_d$ (e.g., either a fit or a peak in the two-dimensional plot) can used to characterize both the fluid type (the bulk diffusivity $D_0$) and pore size (e.g., a surface-to-volume ratio) using relationships, such as those defined by equations 10 and 11. Furthermore, the two-dimensional plot can be analyzed to determine a distribution of bulk diffusivity $D_0$ and pore size. The signal from each plot element (e.g., at a particular $D_s$ and $D_d$ value) is projected onto a one-dimensional bulk diffusivity spectra ($D_0$) and onto a one-dimensional pore size spectra (e.g., surface-to-volume ratio). The diffusion time correlation plot may also be remapped for a two-dimensional plot of bulk diffusivity versus pore size. The diffusion time correlation plot can be used to separate out and identify different components of water and oil in different pore sizes. A diffusion time correlation plot could include additional dimensions, for example a $T_2$ coordinate for a $D_s$-$D_d$-$T_2$ plot.

The method described herein was performed on an avocado sample and a water sample. The avocado sample was cored from the edible portion (mesocarp) of a Haas avocado with a 2.5-mm inner diameter glass tube. This portion of the avocado includes cells averaging 60 μm in diameter, which contain 0.5 to 20 μm diameter oil droplets. The NMR signal of an avocado has multiple relaxation components corresponding to water and oil in different cellular environments. In this case, NMR signal data from water within vacuoles is used to analyze the avocado sample. The vacuole is the water storage compartment of a plant cell. Vacuolar water has the longest $T_2$ relaxation time (e.g., greater than 200 ms) of the other component fluids within the avocado. Thus, the NMR signal from other component fluids (e.g., oil) will have decayed away during the diffusion encoding time (e.g., 240 ms in total). As a fluid contained within a porous media, the vacuolar water signal should have components of both bulk diffusion and restricted diffusion.

An NMR pulse sequence, such as the one shown in FIG. 15, was applied to the avocado and water samples. The NMR pulse sequences included two sets of gradient pulses followed by a CPMG sequence. Additionally, a 180 degree refocusing pulse was spaced between the first pulse and second pulse within each set. The encoding parameters were: $\delta$=4.0 ms, $\Delta$=120 ms, and $2\Delta$=240 ms. The NMR pulse sequence was repetitively applied with various different value of $q_s$ and $q_d$. The values of $q_s$ and $q_d$ spanned between 0 and 82 cm$^{-1}$ for an 11-by-11 sampling array. The q values were calibrated based on the water sample assuming a bulk diffusion constant of $2.2\times10^{-5}$ cm$^2$/s.

Figure 22:
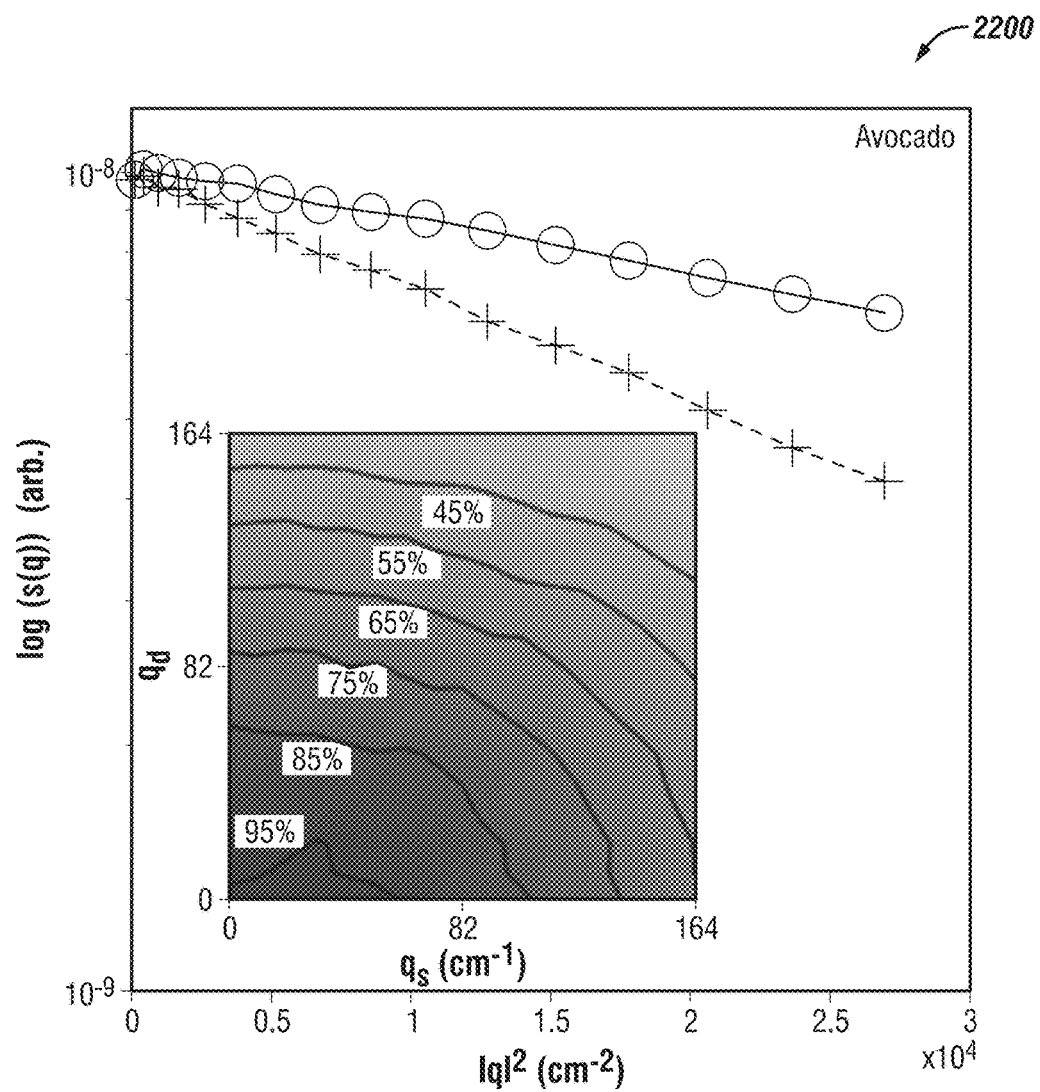
FIG. 22 shows NMR signal data as a function of $q_s$ and $q_d$ for an avocado sample.
Figure 23:
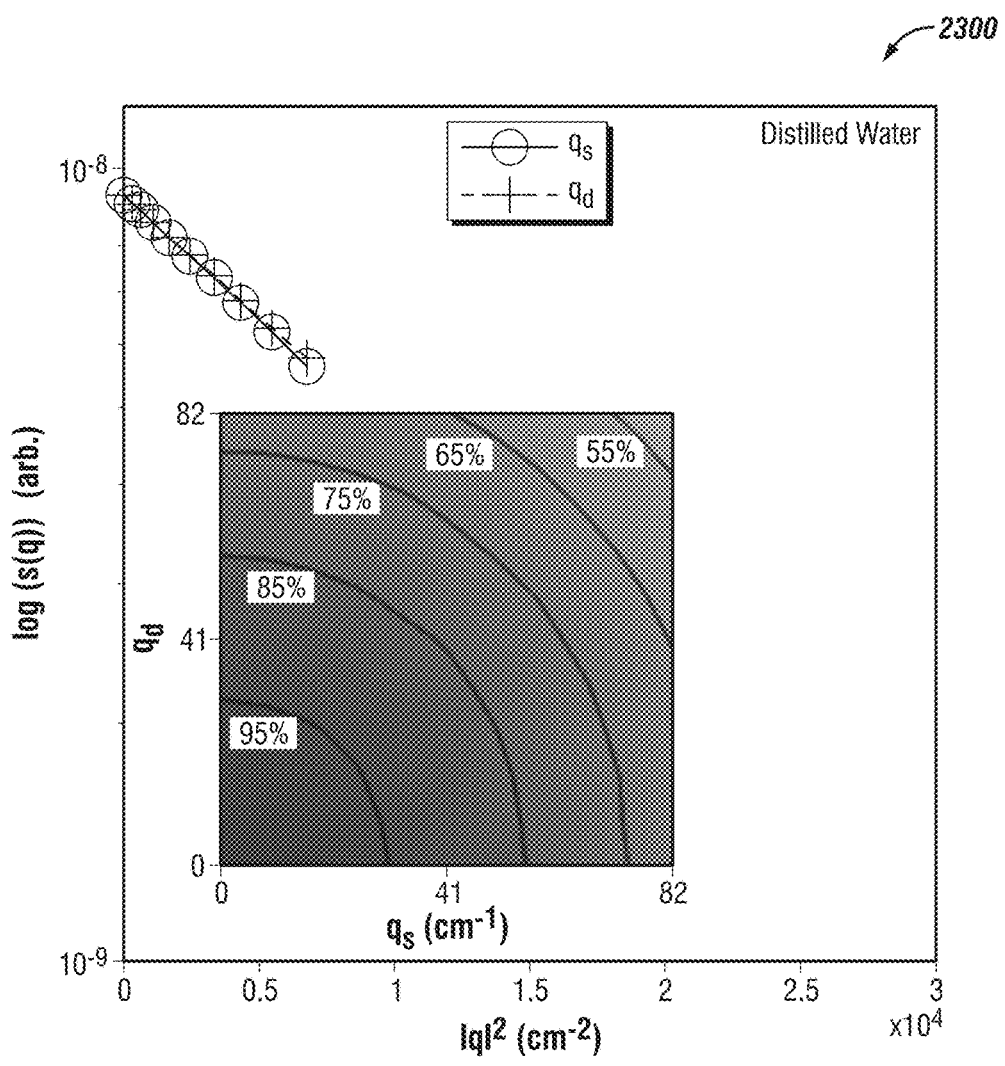
FIG. 23 shows NMR signal data as a function of $q_s$ and $q_d$ for a water sample.

FIG. 22 shows the NMR signal data as a function of $q_s$ and $q_d$ for the avocado sample 2200, while FIG. 23 shows the NMR signal data as a function of $q_s$ and $q_d$ for the water sample 2300. For the water sample, the NMR signal data is radially symmetric in the $q_s$ and $q_d$ plane consistent with free diffusion and the absence of time-dependent diffusion. In contrast, the NMR signal shows a slower decay along the $q_s$ axis than along the $q_d$ axis. This indicates that the measured diffusion coefficient decreases with diffusion time, which indicates the presence of restricted diffusion. Furthermore, the pattern of the decay in the $q_s$ and $q_d$ plane shows that the principle axes are $q_s$ and $q_d$ confirming the form of equation 7. If these were not the principle axes, then the equation would not have this simple form and involve products of $q_s$ with $q_d$ (e.g., $q_s \times q_d$).

Figure 25:
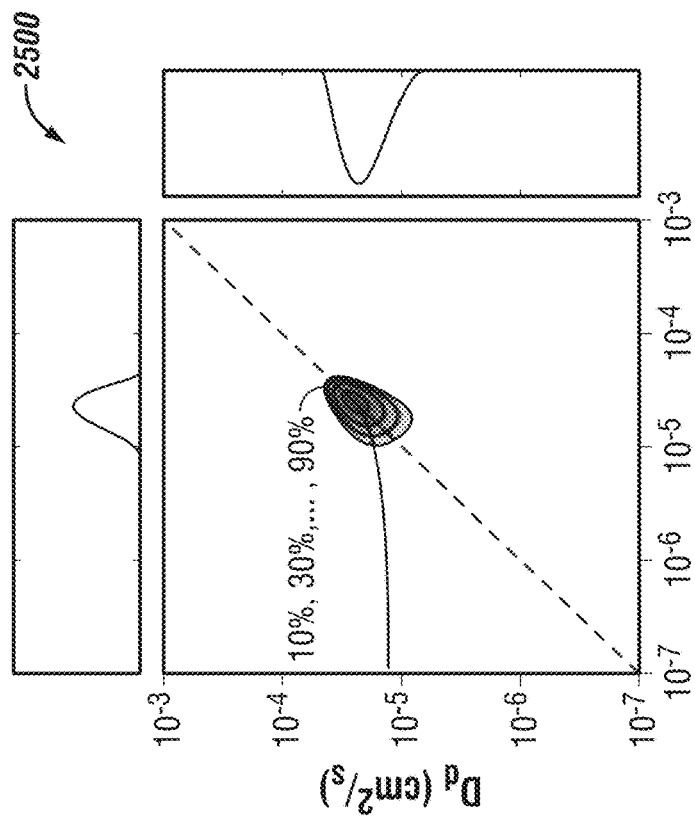
FIG. 25 shows a two-dimensional plot of diffusion coefficients for the water sample.
Figure 24:
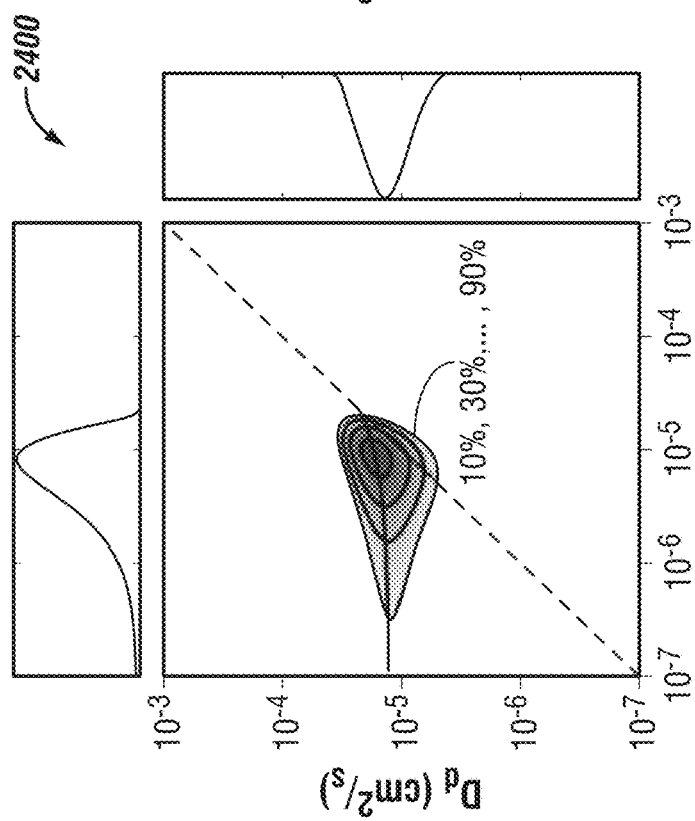
FIG. 24 shows a two-dimensional plot of diffusion coefficients for the avocado sample.

A two-dimensional Laplace inversion was applied to the NMR signal data from the avocado sample and the water sample to produce a two-dimensional plot of diffusion at a first diffusion time ($D_s$) and diffusion at a second diffusion time ($D_d$). FIG. 24 shows the two-dimensional plot of diffusion coefficients for the avocado sample 2400, while FIG. 25 shows the two-dimensional plot of diffusion coefficients for the water sample 2500. FIG. 24 shows off-diagonal components for the avocado sample and FIG. 25 shows that the NMR signal is on-diagonal for the water sample. These results are consistent with restricted and free diffusion for the respective samples. Furthermore, the NMR signal data directly overlays with a curved line corresponding to a restricted diffusion model for water, as defined by equation 9.

The linear mean values of $D_s$ and $D_d$ are (2.2; 2.2) and (0.63; 1.45)$\times10^{-5}$ cm$^2$/s for the water sample and avocado sample, respectively. Applying equations 10 and 11 to the NMR signal data a value of $2.02\times10^{-5}$ cm$^2$/s for the bulk diffusion coefficient ($D_0$) of vacuolar water and a value of 554 cm$^{-1}$ (or a 108 μm spherical diameter) for the pores within the avocado sample are obtained. This diameter is slightly larger than the nominal size of the typical vacuoles of an avocado fruit. This overestimate happens for three reasons. Firstly, the diffusion length of the nuclei was 31 μm (e.g., diffusion length=$\sqrt{2D_0(2\Delta)}$), which is a significant fraction of the pore size (e.g., small $l_r$). The diffusion time could be decreased to determine a better approximation of the pore size. Secondly, plant cells are rectangular in nature and diffusion is fully constrained within this compartment. Thus the measured surface-to-volume ratio should correspond to a smaller length than that of a spherical cell. Overall, the properties obtained for the avocado and water sample agreed with the cellular geometry in an avocado fruit.

A wide variety of diffusion encoding gradient sequences exist that can measure different aspects of diffusive motion or to address various experimental limitations. In the PFG, an applied pair of gradient pulses (e.g., a pair of rectangular pulses) can be considered as one of many ways to modulate the gradient strength as a function of time (g(t)), which will be referred to herein as the gradient waveform, and there are many different possible functions that can be utilized. For example, one strategy to characterize small pores is to use oscillating gradients (see Parsons et al. "Temporal Diffusion Spectroscopy: Theory and Implementation in Restricted Systems Using Oscillating Gradients" MRM 55:75-84 (2006)). In this way, the measurement is sensitive to short diffusion times, so to characterize small pores, and achieves adequate signal modulation by repeating this encoding. To compute the signal from these and other gradient waveforms, there are multiple similar or analogous formulas. One such formula uses the Fourier transform of the gradient waveform to compute the second moment of the signal (see Stepišnik et al. "Spectral characterization of diffusion in porous media by the modulated gradient spin echo with CPMG sequence." JMR. 182, 195-199 (2006)). In this formulation, for the second order moment approximation of the signal:

$$E \approx E_0 e^{-\beta}, \quad (17)$$

the term $\beta$ is computed as $$\beta = \frac{\gamma^2}{2\pi} \int_{-\infty}^{\infty} d\omega G(\omega) I_z(\omega) G^*(\omega). \quad (18)$$

This formulation depends on the Fourier transform of the effective gradient strength applied in time (gradient waveform), $$G(\omega) = \int dt \, g_{\mathit{eff}}(t) e^{-i\omega t} \quad (19)$$

and of the displacement autocorrelation function $$I_z(\omega) = 1/\pi \int_{-\infty}^{\infty} dt \langle \Delta z(t) \Delta z(0) \rangle e^{-i\omega t} \quad (20).$$

The displacement autocorrelation function is the time average (denoted by $\langle \, \rangle$) over the particle's entire trajectory of its displacement from its mean path $$\Delta z(t_0) = z(t_0) - \langle z(t_0) \rangle \quad (21)$$

correlated to the displacement at a fixed relative time ($\Delta z(t+t_0)$). This autocorrelation function is simply a different characterization of diffusion. A conversion from $I_z(\omega)$ to the time dependent diffusion coefficient may be computed according to Stepišnik et al. as $$D(t) = \frac{2}{\pi t}\int_0^\infty d\omega I_z(\omega)[1 - \cos(\omega t)] \qquad (22)$$

One of the uses of this frequency description is to design pulse sequences with superior robustness to "background gradients." (see G. Zheng et al. "Suppression of Background Gradients in ($B_0$ Gradient-Based) NMR Diffusion Experiments" Concepts in Magnetic Resonance 30A(5) 261-277 (2007)). Background gradients are typically unintentional gradients in the magnetic field that can be present due to a variety of experimental issues such as imperfections in the NMR magnet or magnetism of the sample. Where $F_a$ and $F_o$ are defined to be the Fourier transforms of the effective gradient from the applied and the background gradient, they find that the term $\beta$ is:

$$= -\frac{1}{\pi}D\int_0^\infty [|F_a'|^2 + 2Re(F_a'F_0'^*) + |F_0'|^2]d\omega \qquad (23)$$

The $|F_0|^2$ value has a fixed effect on the signal and Zhang et al. describe methods to minimize this value. More problematic is the term $Re(F_a F_o)$, since it means that the presence of the background gradient affects the encoding of the applied gradient pulse. Zhang et al. note that this cross-term can be minimized by ensuring that the spectra of the effective applied and background gradient are separate (e.g., intense at different frequencies).

In accordance with example implementations of this application, multiple ways to design overlapping diffusion gradients are provided and can be utilized in an analogous manner as $q_s/q_d$. These methods may be based, for example, on symmetry, blurring (or convolution), spectral and phase separation, and orthogonalization. An aspect of the design of overlapping diffusion encoding gradients in accordance with example implementations is to provide that the gradients are decoupled such that, for example, the application of one of the diffusion encodings does not affect the encoding of the other.

Below is provided an evaluation of the general criteria for gradient decoupling in accordance with some implementations. From this basic expression, various techniques to develop decoupled gradients and their associated applications may be developed, and some examples are provided below. The primary application of these criteria is to design and construct the overlapping gradient waveforms such as those described in the foregoing description. In the following, any gradient terms are assumed to refer to effective gradients (i.e., the equivalent applied gradient pulse in the absence of refocusing RF pulses) unless explicitly noted otherwise.

General Criteria for Gradient Decoupling

Figure 26:
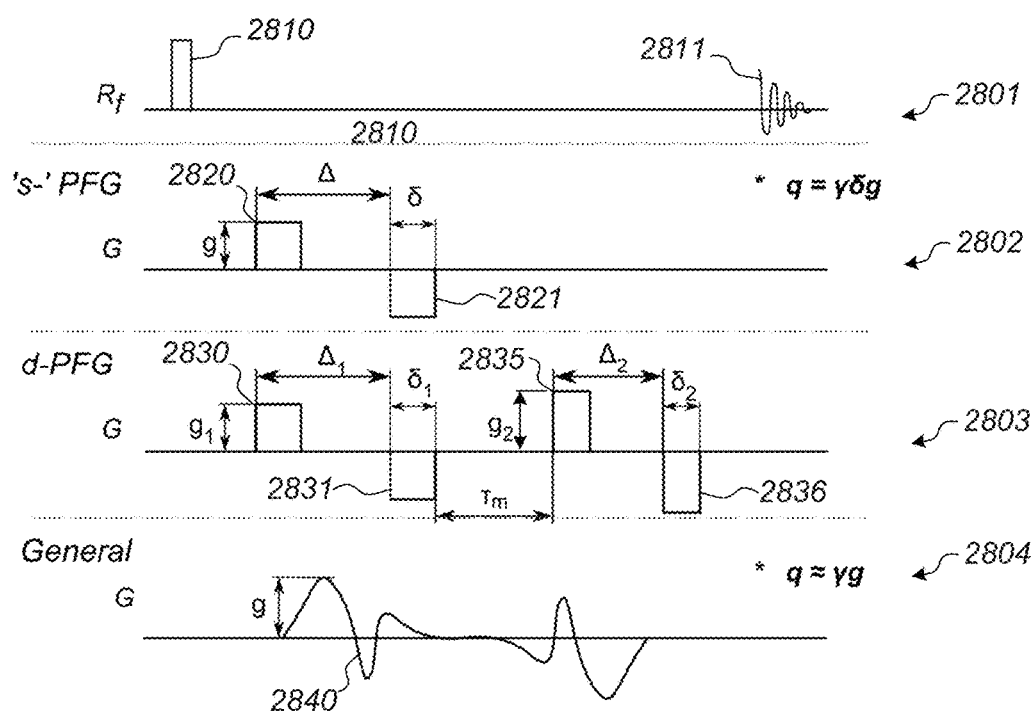
FIG. 26 shows a pulse sequence, RF signal acquisition, and diffusion encoding gradients.

FIG. 26 shows a pulse sequence and RF signal acquisition at 2801, an ordinary single or "s"-PFG at 2802, a double PFG (d-PFG) at 2803, and a general waveform PFG at 2804. For both the single PFG 2802, the d-PFG 2803, and the general waveform PFG 2804, the RF pulse sequences also include, referring to 2801, the initial RF pulse 2810 to excite the NMR signal and a later RF signal acquisition 2811 at a substantially similar frequency. The single PFG 2802 uses a pair of matched gradient pulses 2820 and 2821 each defined by a width in time ($\delta$) and an amplitude (g) corresponding to the applied magnetic field gradient. An area parameter, $q=\gamma\delta g$, describes the overall strength of the encoding performed by the gradient pulses, where $\gamma$ is the gyromagnetic ratio, a fundamental constant of the nuclei detected. The PFG is further described by the delay between the gradient pulses ($\Delta$) which corresponds to the timescale over which the diffusion is measured. The d-PFG is an extension of the ordinary 'single' PFG 2802, the d-PFG 2803 including, in addition to a first pair of matched gradient pulses 2830 and 2831, a second independently varied PFG (with gradient pulses 2835 and 2836) applied after the first. This introduces another type of parameter, the mixing time $T_m$, which parameterizes the separation in time between the two PFG pairs 2830/2831 and 2835/2836. Referring to 2804, diffusion encoding gradients do not have to take the form of paired rectangular pulses as with the PFGs 2802 and 2803, as long as the integral of the gradient waveform 2840 evaluates to 0. Then the area parameterization, q, as with the standard PFG techniques is still proportional to the amplitude of the pulse, g. As shown at 2804, the pulses of the waveform 2840 are non-rectangular.

For any gradient waveform $g_a(t)$, there is an associated area parameter $q_a$ proportional to the amplitude of the gradient waveform and is analogous to the area parameter q used to describe the diffusion encoding in the PFG sequence such as shown at 2804. If there is also some other gradient waveform $g_b(t)$ (with associated area parameter $q_b$) that is applied along with $g_a(t)$, for the second order approximation of the signal the exponent $\beta$ will take the general form:

$$\beta = Q_a q_a^2 + Q_b q_b^2 + Q_{ab} q_a q_b \qquad (24)$$

where $Q_a$, $Q_b$, and $Q_{ab}$ are sensitive to diffusion and the length of time of the gradient waveform. For example, when characterizing the double-PFG by $q_1$ and $q_2$, with $\tau_m=0$, then $Q_1=\Delta D(\Delta)$, $Q_2=\Delta D(\Delta)$, and $Q_{12}=2\Delta[D(2\Delta)-D(\Delta)]$.

According to this general equation, when $Q_{ab}\neq 0$, a change in the strength of one gradient (e.g., $q_a$) will affect the encoding strength of the other gradient (e.g., $q_b$) through the cross-term $Q_{ab}q_a q_b$. Thus, the decoupling criteria may be considered finding the gradient waveforms $g_a(t)$ and $g_b(t)$ such that $Q_{ab}=0$. Then, the application of $q_a$ will not affect the encoding strength of $q_b$ and vice versa.

Equation (24) is also used in the similar context of background gradient cross terms (see Zheng et al.) (Equation (23)) when describing the basic effect on background gradients on a single diffusion measurement with a similar purpose of minimizing $Q_{ab}$. However, $q_b$ in that context is a fixed term corresponding to the background gradient that is dependent on the sample and is not generally under the control of the experimentalist.

To determine the general decoupling criteria, it is considered to apply two arbitrary gradient waveforms, $ag_a(t)$ and $bg_b(t)$, and substitute this into Stepišnik et al.'s formula (Equation (18)) for $\beta$. Here, each gradient waveform is characterized by a scalar (a and b) to represent modulating their amplitudes independently between measurements, and as a function of time ($g_a(t)$ and $g_b(t)$), to describe the modulations of the gradient strength within a single encoding that characterizes each. In some examples, an implicit constraint is placed on $g_a(t)$ and $g_b(t)$ as having zero area (e.g., $\int dt\, g(t)=0$), so that, for example, they are suitable for making some measure of diffusion.

To substitute into Stepišnik's formula (Equation (18)), the Fourier transform of the applied gradient is substituted for. The applied gradient as a function of time is simply $g(t)=ag_a(t)+bg_b(t)$. Because the Fourier transform is a linear operation, the Fourier transform of the applied gradient is the linear combination of the Fourier transforms of the two constituent gradients $G(\omega)=aG_a(\omega)+bG_b(\omega)$. Thus, the second order term evaluates to:

$$\beta = \frac{\gamma^2}{2\pi}\int_{-\infty}^{\infty}d\omega(aG_a(\omega)+bG_b(\omega))I_z(\omega)(aG_a^*(\omega)+bG_b^*(\omega)) \quad (25)$$

$$\beta = \frac{\gamma^2}{2\pi}\int_{-\infty}^{\infty}d\omega I_z(\omega)(a^2 G_a(\omega)G_a^*(\omega) + \quad (26)$$
$$b^2 G_b(\omega)G_b^*(\omega) + ab(G_a(\omega)G_b^*(\omega) + G_b(\omega)G_a^*(\omega))]$$

Since the q values are proportional to the amplitude of the applied gradient, the terms in this expression may be converted into the general formulation for β in accordance with Equation (24). Thus:

$$q_a^2 Q_a = a^2 \frac{\gamma^2}{2\pi}\int_{-\infty}^{\infty} d\omega I_z(\omega)[G_a(\omega)G_a^*(\omega)] \quad (27)$$

$$q_b^2 Q_b = b^2 \frac{\gamma^2}{2\pi}\int_{-\infty}^{\infty} d\omega I_z(\omega)[G_b(\omega)G_b^*(\omega)] \quad (28)$$

$$q_a q_b Q_{ab} = ab\frac{\gamma^2}{2\pi}\int_{-\infty}^{\infty} d\omega I_z(\omega)[G_a(\omega)G_b^*(\omega) + G_b(\omega)G_a^*(\omega)] \quad (29)$$

Because a and b are varied to perform the experiment, they are allowed to take on any real value. Thus in some examples, whether the term $Q_{ab}$ is zero, which determines if gradients are decoupled, solely depends on the Fourier transform of their associated modulation profiles, $G_a(\omega)$ and $G_b(\omega)$. Furthermore, since $I_z(\omega)$ is a property that generally varies between different samples, for the integral to always evaluate to zero, the term dependant on $G_a(\omega)$ and $G_a(\omega)$ is to be zero for each ω. Thus, the general decoupling criteria may be expressed as:

$$0 = G_a(\omega)G_b^*(\omega)+G_b(\omega)G_a^*(\omega), \forall \omega \quad (30a)$$

which may also be expressed as $$\frac{G_a(\omega)}{G_a^*(\omega)} = -\frac{G_b(\omega)}{G_b^*(\omega)}, \forall \omega. \quad (30b)$$

As an example, the criteria are applied to the $q_s$ and $q_d$ waveforms described in the description set forth above:

$$G_s(\omega)=2i\sin(2\Delta\omega) \quad (31)$$

$$G_d(\omega)=2(1-\cos(2\Delta\omega)) \quad (32)$$

which satisfy the criteria as shown below:

$$\frac{2i\sin(2\Delta\omega)}{-2i\sin(2\Delta\omega)} = -1, \frac{2(1-\cos(2\Delta\omega))}{2(1-\cos(2\Delta\omega))} = 1 \quad (33)$$

Thus; the determination of whether two gradients are decoupled is now reduced to evaluating a simple algebraic formula.

The major advantage of this formulation is that the basic properties and symmetries of the Fourier representation will allow us to make very general statements on how to make diffusion encoding gradients decouple. Unlike prior techniques, these will allow for the design of decoupled gradients without the explicit calculation of their effect on the diffusion signal.

Before continuing, the following properties of the Fourier transform which are used later are noted:

Given that $f(t)$ is a real function because it describes the modulation in time of the applied gradient (e.g. the function just returns real values, not complex or imaginary numbers), its Fourier transform $F(\omega)$ has the following properties.

1. $F^*(\omega)=F(-\omega)$
2. If $f(t)$ is also even (e.g. $f(t)=f(-t)$), then $F(\omega)$ is real valued and even.
3. If $f(t)$ is also odd (e.g. $-f(t)=f(-t)$), then $F(\omega)$ is purely imaginary and odd.

Finally, the following normalization convention is also used for the Fourier Transform:

$$F(\omega)=\int_{-\infty}^{\infty}dt f(t)e^{-i\omega t} \quad (34)$$

Symmetry Criteria for Gradient Decoupling

Figure 27:
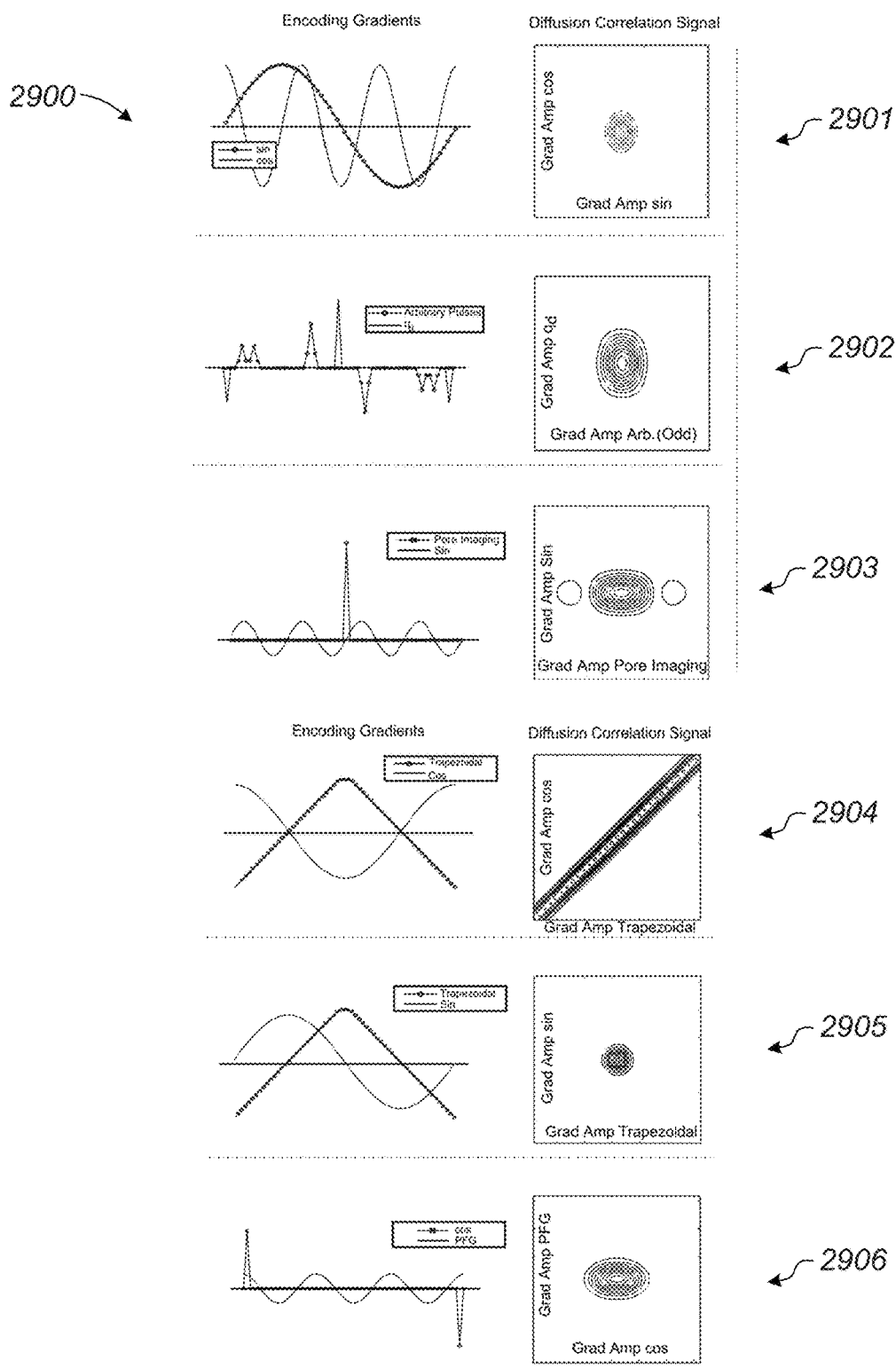
FIG. 27 shows evaluation of even/odd decoupling criteria with numerical modeling for encoding of restricted diffusion in a parallel plate pore using a simulation library.

The symmetry criteria for gradient decoupling, is that any gradient with even symmetry will decouple with another gradient with odd symmetry about the same point (see FIG. 27). Specifically, given that:

$$g_{even}(t-t_0)=g_{even}(-(t-t_0)) \quad (35a)$$

$$g_{odd}(t-t_0)=-g_{odd}(-(t-t_0)) \quad (35b)$$

(where both gradient waveforms are symmetric about time $t_0$), $g_{even}$ and $g_{odd}$ should decouple and be appropriate for use for overlapping diffusion encoding measurements and diffusion correlation measurements. This allows for the immediate identification and design of decoupled gradient waveforms and is robust as demonstrated in numerical simulations as presented at 2901, 2902, 2903, 2904, 2905, and 2906 in FIG. 27. FIG. 27 shows the evaluation of the even/odd decoupling criteria with numerical modeling for the encoding of restricted diffusion in a parallel plate pore using the simulation library cited in D. S. Grebenkov, "NMR survey of reflected Brownian motion." Rev. Mod. Phys. 79, 1077-1137 (2007). In these plots, decoupling exhibits as mirror symmetry in the simulated signal about the two encoding axes. It is shown clearly for a variety of diffusion encoding gradients decoupled by odd/even symmetry: between (a) referring to 2901, sine and cosine, (b) referring to 2902, a multiple pulse encoding waveform with odd symmetry and $q_d$, (c) referring to 2903, sine and a pore imaging waveform, (d) referring to 2905, a trapezoidal and sine waveform, and (e) referring to 2906, cosine and ordinary gradient waveform. Referring to 2904, even if the waveforms are similar between the cosine and sine waveforms, the cosine waveform fails to decouple with the trapezoidal encoding gradient whereas the sin waveform does not.

The odd/even criteria can be proven from the decoupling criteria and the properties from the Fourier transform. Without loss of generality, the time axis t can be defined such that $t_0=0$. Then $$g_{even}(t)=g_{even}(-t) \quad (36)$$

$$g_{odd}(t)=-g_{odd}(-t).$$

Given Fourier transform relations 2 and 3, their Fourier transforms have the same symmetry.

$$G_{even}(\omega)=G_{even}(-\omega) \quad (37)$$

$$G_{odd}(\omega)=-G_{odd}(-\omega).$$

Applying the decoupling criteria and Fourier transform:

$$G_{even}(\omega)G^*_{odd}(\omega) + G_{odd}(\omega)G^*_{even}(\omega) = \quad (38)$$
$$G_{even}(\omega)G_{odd}(-\omega) + G_{odd}(\omega)G_{even}(-\omega) =$$
$$-G_{even}(\omega)G_{odd}(\omega) + G_{odd}(\omega)G_{even}(\omega) = 0$$

Thus, the gradients decouple.

Variations to $q_s$ and $q_d$ for Diffusion/Diffusion Correlation:

For the $q_s$ (odd) and $q_d$ (even) waveforms described above ($\Delta_1=\Delta_2$), the symmetry relation immediately indicates that they are decoupled independent of $\tau_m$ and hence are appropriate for diffusion correlation measurements.

This relation also shows that this sequence is robust to experimental variations. Some example formulas set forth above assume that the gradient pulses have finite area yet negligible width, and did not strictly establish decoupling for finite pulse widths and rely on numerical and experiment confirmation. In accordance with example implementations, however, as long as the odd/even symmetries are maintained (see, e.g, FIG. 29A), implementations with wide and shaped gradient pulses (see, e.g., FIG. 29B) will still strictly decouple. In application, wider pulse widths can help compensate for limited gradient strength and shaped gradient pulses can help avoid experimental limits to rapidly changing the gradient strength. Also, this odd/even criteria demonstrates that any mixing time (see, e.g., FIG. 29C) is viable, not just small mixing times such as may be described in some other examples.

The $q_s/q_d$ sequence can also be modified to correlate any ratio of diffusion times for better pore size characterization and improved contrast between different components in a heterogeneous sample. Independently varying the encoding time is also allowed, as long as the relative odd/even symmetry is maintained, as shown in FIGS. 29D and 29E. The original $q_s/q_d$ implementation described in above sections with regard to the rectangular PFG sequences correlate diffusion over two times differing by a factor of 2. By increasing this ratio, there will generally be greater contrast between the two encodings in the correlation measurement. This increased contrast arises because there is typically a greater difference in the apparent diffusion coefficient as the difference between the two diffusion times increases. To implement, the modification involves changing the delay time between pulses ($\Delta$) for either $q_s$ or $q_d$, while maintaining the relative odd/even symmetry; for example by decreasing the spacing between pulses in $q_d$ while maintaining the same center (FIG. 29E).

Diffusion/Diffusion Correlations with Oscillating Gradients:

Oscillating gradients (see, e.g., Parsons et al. "Temporal Diffusion Spectroscopy: Theory and Implementation in Restricted Systems Using Oscillating Gradients" MRM 55:75-84 (2006)) present another methodology in order to better characterize smaller pores. Pore size sensitivity depends on the frequency of the oscillating gradient. To correlate different oscillating gradient measurements, the symmetry rule may be used to design the pairs of decoupled diffusion encoding gradients. For example, using a sin/cos (odd/even) combination will decouple independent of the two modulation frequencies or number of periods used (FIGS. 30A, 30B, 30C, and 30D) as long as the symmetries are maintained. In some examples, designing each of the gradients as two pairs of sin pulses, where the second pulse is a copy of the first in one and has the opposite sign in the other, will also maintain decoupling by the odd/even symmetry criteria (FIG. 30D).

Diffusion/Diffusion Correlations with Shaped Gradients:

The previous two applications of the symmetry rule to generate decoupled gradients both decoupled similar types of gradient encoding (PFG and oscillating gradient). It should be appreciated that different types of gradient measurements can be decoupled with each other in a diffusion correlation measurement. For example, referring to FIG. 31A, an ordinary PFG encoding gradient (for characterizing larger pores) can be decoupled with an oscillating gradient (for characterizing smaller pores) as long as the oscillating gradient has even symmetry.

Another example, referring to FIG. 31B, is an even gradient waveform for diffusion pore imaging being combined with a PFG encoding for additional contrast (see T. A. Kuder et al. "Diffusion Pore Imaging by Hyperpolarized Xenon-129 Nuclear Magnetic Resonance" PRL 111, 028101 (2013)). A PFG with a short diffusion encoding time may be used for "edge contrast" to better identify multiple pore shapes. Further, referring to FIG. 31C, a PFG with a long diffusion encoding time may be used to remove signal from open pores or from free diffusion, which is not correctly handled by the traditional pore imaging technique.

Eliminating Background Gradient Cross Terms.

Figure 32:
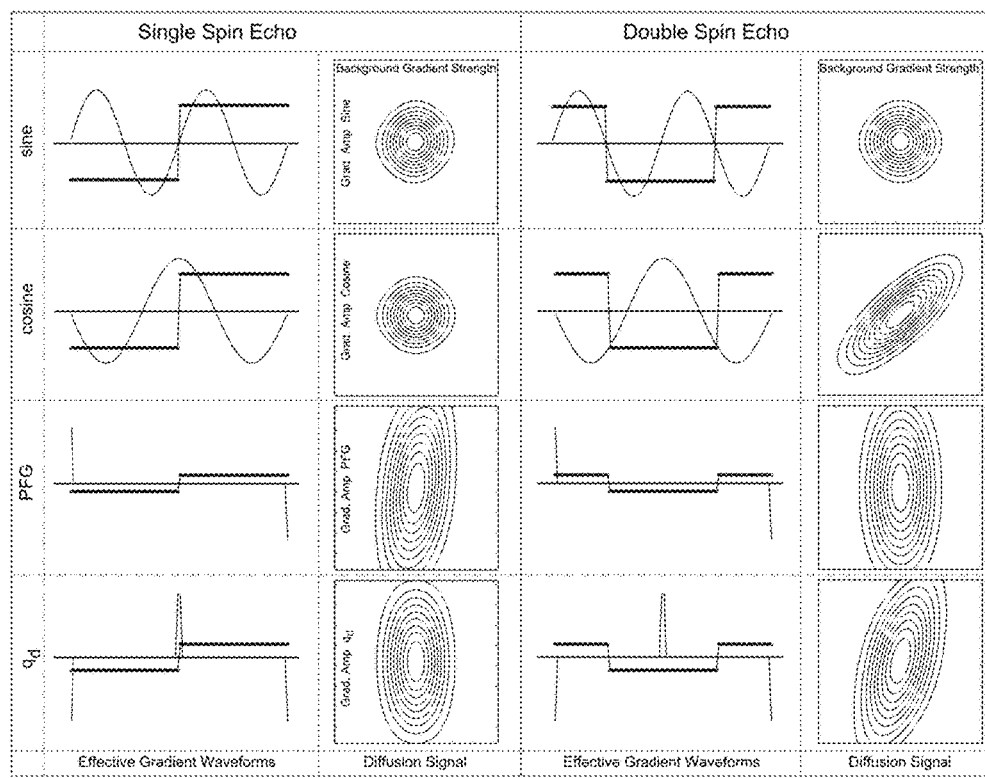
FIG. 32 shows evaluation of the presence of the background gradient cross terms using the odd/even symmetry criteria.

Due to imperfections in the magnet used in the NMR device or the magnetic properties of the sample, there can be a constant magnetic field gradient. These are commonly referred to as background or internal gradients depending on the source. For any diffusion measurement, such as the PFG, the background gradient acts as a second pulse ('$g_b$'). In Equation (23), $Q_b$ can typically be made small by minimizing the background gradient strength and CPMG refocusing. However, even a small cross-term $Q_{ab}$ can become significant for strong applied gradient pulses ($q_a$), thus hindering the analysis. Pulse sequences that zero this cross-term are commonly used and are applied to analyzing porous media (W. S. Price "Pulsed-Field Gradient Nuclear Magnetic Resonance as a Tool for Studying Translational Diffusion: Part II. Experimental Aspects." Concepts in Magnetic Resonance 10(4) 197-237 (1998)). The odd/even symmetry criteria here can be used to quickly design such pulse sequences. In FIG. 32, the concept is illustrated with a single and a double spin echo sequence against oscillating gradient and PFG techniques. It should be noted that this approach would also apply to decoupling a great variety of shaped gradient waveforms from the background gradient; and that bi-polar techniques (Zheng et al, Price et al) are frequently unneeded to address this specific issue.

Blurring (Convolution) Decoupling Criteria

The blurring (convolution criteria) allows the design of decoupled gradients $g_a$, and $g_b$, by modifying a pair of gradients that are already known to decouple $g_a$ and $g_b$. There are two versions to generate new pairs of decoupled gradients; the first allows for the waveforms to be blurred by any shape, the second allows for the blurring of just one of the gradients.

Given that $g_a(t)$ and $g_b(t)$ are a pair of decoupled diffusion gradient waveforms:
1. Given any square integrable blurring function $c(t)$, $g_a(t)=(c*g_a)(t)$ and $g_b(t)=(c*g_b)(t)$ also decouple where (*) denotes convolution (blurring).
2. Given any square integrable even blurring function $c(t)$, $g_a(t)=(c*g_a)(t)$ and $g_b(t)$ also decouple where (*) denotes convolution (blurring).

Figure 33:
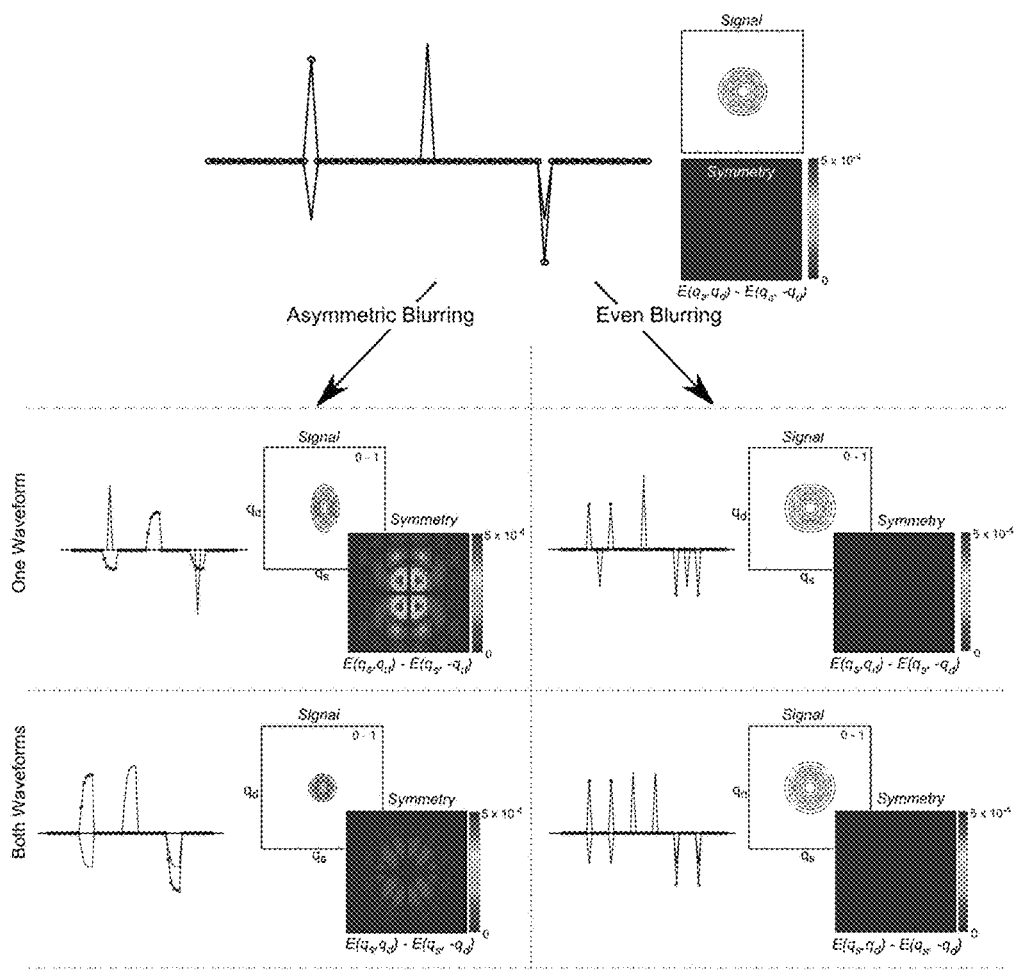
FIG. 33 shows the effect of blurring gradient waveforms on decoupling.

An example of how blurring preserves decoupling is shown in FIG. 33. FIG. 33 plots simulations of the gradient pair ($q_s, q_d$) which are known to decouple, and these gradient waveforms are blurred by an even function and an asymmetric function including an exponential equilibration. The even function is simply a split/pair of peaks to represent an example of making a new sequence based on $q_s$ and $q_d$ whereas the asymmetric blurring function is an exponential settling function to mimic a realistic gradient rise time. Each portion of the figure shows the gradient waveform's shape and its simulated signal (scaled to span 0 to 1) as a function of the amplitude of the two simultaneously applied gradients. Symmetry breaking (and hence loss of decoupling) is illustrated by plotting the signal subtracted from its mirror image ($E(q_s, q_d) - E(q_s, -q_d)$). Non-zero signals in these symmetry plots indicate deviations from mirror symmetry. For these plots, the shading scale spans values from 0 to $5 \times 10^{-4}$ to highlight minor deviations. From these simulations, whether one or both gradient waveforms are blurred by the even function doesn't matter and decoupling is maintained. Also, both gradient waveforms are blurred for an asymmetric blurring to maintain decoupling. The small residual remaining in this example is likely due to small numerical errors in the signal calculation and indicates that this property is less robust to small numerical errors. However, as the errors are less than $1 \times 10^{-4}$, regardless these would not typically be experimentally significant.

To prove, let $c_a(t)$ and $c_b(t)$ be the blurring functions applied to the decoupled gradient waveforms $g_a(t)$ and $g_b(t)$. By the convolution theorem, the Fourier transforms of the blurred gradient waveforms $g_{a'}(t) = (c*g_a)(t)$ and $g_{b'}(t) = (c*g_b)(t)$ are $$G_{a'}(\omega) = C_a(\omega) G_a(\omega) \quad (39)$$

$$G_{b'}(\omega) = C_b(\omega) G_b(\omega) \quad (40)$$

where $C_a(\omega)$ and $C_b(\omega)$ are the Fourier transforms of the blurring functions. Applying the decoupling criteria to the blurred gradient waveforms provides:

$$C_a(\omega) G_a(\omega) C_b^*(\omega) G_b^*(\omega) + C_b(\omega) G_b(\omega) C_a^*(\omega) G_a^*(\omega) \quad (41)$$

For the first blurring criteria, the two blurring functions are identical. These blurring terms factor out leaving the decoupling criteria for $g_a(t)$ and $g_b(t)$ which by definition are decoupled. Written out, the decoupling criteria for $g_{a'}(t)$ and $g_{b'}(t)$ then evaluates to $$= C(\omega) C^*(\omega) [G_a(\omega) G_b^*(\omega) + G_b(\omega) G_a^*(\omega)] = C(\omega) C^*(\omega)[0] = 0 \quad (42)$$

and so the blurred pair of gradient waveforms also decouple.

For the second blurring criteria, the first blurring function is even. Thus, $$C_a^*(\omega) = C_a(-\omega) = C_a(\omega) \quad (43).$$

Since no blurring is applied to the second pulse, this is equivalent to having $C_b(\omega) = 1$. In this case, the remaining blurring terms again factor out leaving the decoupling criteria for $g_a(t)$ and $g_b(t)$, which by definition are decoupled. Written out, Equation (41) in this case evaluates to $$= C_a^2(\omega) [G_a(\omega) G_b^*(\omega) + G_b(\omega) G_a^*(\omega)] = C_a^2(\omega)[0] = 0 \quad (44)$$

Robust Decoupling with Non-Ideal Pulses

Experimentally, when an NMR instrument applies a gradient pulse, there is a finite time for it to rise and fall to its set values resulting in an asymmetric gradient pulse (P. T. Callaghan "Principles of Nuclear Magnetic Resonance Microscopy", W. S. Price. "Pulsed-field gradient nuclear magnetic resonance as a tool for studying translational diffusion: Part II. Experimental aspects." Concepts in Magnetic Resonance Vol 10 Iss 4 (1998)). For an ideal gradient pulse sequence, that's been designed to be decoupled by another technique, this frequently breaks the original criteria (e.g. for $q_s/q_d$ it's the odd/even symmetry). The first blurring criteria means that as long as the "ideal" sequence is decoupled and the same experimental blurring occurs for each of the pulses, this non-ideal implementation will still decouple (FIG. 33: both asymmetrically decoupled). This approach, simply not adjusting for gradient rise and fall, has several features. It is far simpler to implement than the careful optimization of instrumentation to minimize gradient rise and fall time or to intentionally shape gradient pulses to minimize the effect. Furthermore, by tolerating for these gradient artifacts, it allows for the application of shorter and longer gradient pulses and delays for improved diffusion measurements for a given instrument's performance.

Correlating Diffusion Measurements with Repetitive Sequences

Figure 34A:
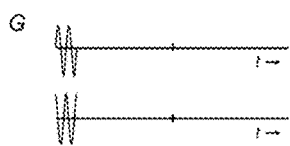
FIGS. 34A and 34B show repetition of gradient waveforms to increase encoding strength and maintain decoupling/independent encoding modes.
Figure 35A:
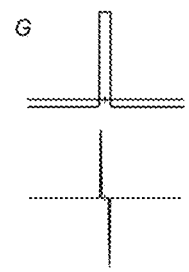
FIGS. 35A and 35B show repetition of a single gradient waveform to increase encoding strength and maintain decoupling/independent encoding modes.
Figure 34B:
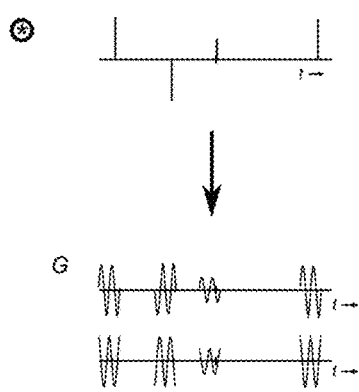
Figure 35B:
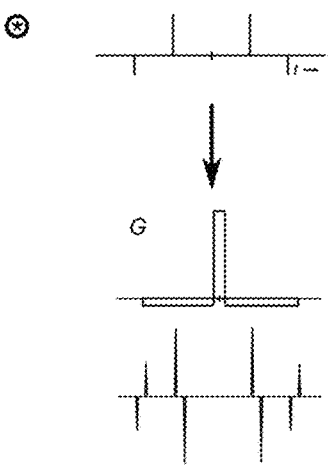
Figure 36A:
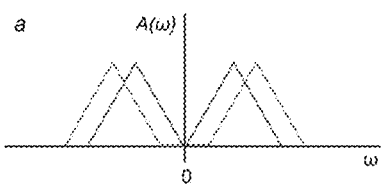
FIGS. 36A to 36E show designs of multidimensional diffusion-diffusion decoupling experiments and the constraints on their construction placed by the frequency criteria.
Figure 36B:
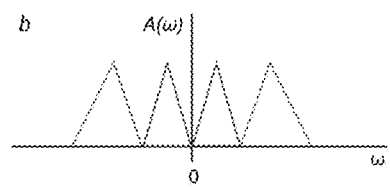
Figure 36C:
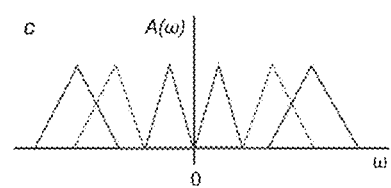
Figure 36D:
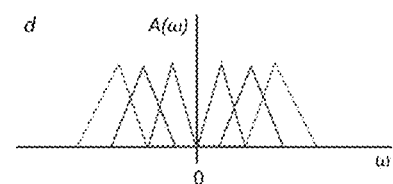
Figure 36E:
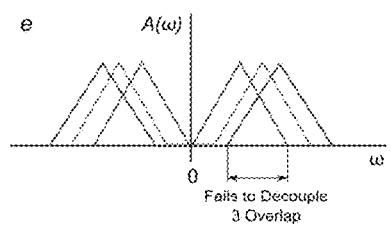

A given pair of encoding gradients for diffusion correlation, $g_a(t)$ and $g_b(t)$, may not be able to experimentally give sufficient signal modulation to characterize a sample given limitations in the gradient strength available. One of the ideas underlying oscillating gradient techniques (J. Xu, M. D. Does, J. C. Gore, "Sensitivity of MR diffusion measurements to variations in intracellular structure: effects of nuclear size." Magn. Reson. Med. 61 (2009) 828-833) is to increase the signal modulation and largely measure the same desired aspect of diffusion by repeating the gradient waveform multiple times. The blurring criteria means that this strategy may also be applied to diffusion correlation measurements. The first version of the criteria means that the use of any sort of repetition pattern will maintain decoupling as long as both gradient waveforms use the same repetition pattern (as defined by a blurring operation; see FIGS. 34A and 34B). If the enhancement is needed for just one of the gradients, the second blurring criteria means that the decoupling will be maintained as long as the blurring function describing the repetition of that one gradient is "even" (see FIGS. 35A and 35B).

Spectral and Phase Separation

Another pair of criteria to test decoupled gradient waveforms is to directly compare their Fourier transforms or in other words spectra. These criteria allow one to furthermore determine if more than two gradient waveforms can be simultaneously decoupled. The first of the criteria involves comparing the amplitude of the two gradient spectra; the second, the complex phase of the two spectra. To describe and prove these criteria, the gradient spectrum is represented as a polar function $G(\omega)$: including a function that is constructed from a positive real valued function of amplitude $A(\omega) \geq 0$ and a real valued function of the phase $\phi(\omega)$:

$$G(\omega) = A(\omega) e^{-i\phi(\omega)} \quad (45)$$

The spectral separation criterion is that:

$$A_a(\omega) A_b(\omega) = 0 \quad (46)$$

Since strictly obeying this criterion may be difficult, it is instead sufficient to substantially separate them (e.g. $A_a(\omega) A_b(\omega) \ll \varepsilon$) such that the cross term is insignificant relative to the desired encodings (e.g. $Q_a q_{a,max}^2 \gg Q_{ab} q_{a,max} q_{b,max}$ and $Q_b q_{b,max}^2 \gg Q_{ab} q_{a,max} q_{b,max}$).

Where the spectra overlap, and what Zheng et al missed, is that decoupling is still possible given that it obeys the phase separation criterion:

$$\phi_a - \phi_b = \pm \frac{\pi}{2} \quad (47)$$

For this second rule, phases $\phi$ that are $2\pi$ radians apart are considered to describe the same angle.

For example, the spectra of $q_s/q_d$ overlap but decouple according to the phase criteria:

$$A_s(\omega) = 2|\sin(2\Delta\omega)| \quad \phi_s(\omega) = \begin{cases} \pi/2 & \sin(2\Delta\omega) \geq 0 \\ -\pi/2 & \sin(2\Delta\omega) < 0 \end{cases} \quad (48)$$

$$A_d(\omega) = 2|1 - \cos(2\Delta\omega)| \quad \phi_s(\omega) = 0$$

Generally, except for oscillating gradient sequences, the spectra for the gradients used in diffusion sequences will overlap and instead obey the phase criterion. This has implications for developing multidimensional diffusion correlation experiments and eliminating background gradient cross terms.

As verification, Substituting the polar representation into the general decoupling criteria (eq 10a) yields:

$$A_a(\omega)A_b^*(\omega)e^{-i[\phi_a(\omega)-\phi_b(\omega)]} + A_b(\omega)A_a^*(\omega)e^{+i[\phi_a(\omega)-\phi_b(\omega)]} = \quad (49)$$
$$A_a(\omega)A_b(\omega)e^{-i[\phi_a(\omega)-\phi_b(\omega)]} + A_b(\omega)A_a(\omega)e^{+i[\phi_a(\omega)-\phi_b(\omega)]} =$$
$$A_a(\omega)A_b(\omega)\{e^{-i[\phi_a(\omega)-\phi_b(\omega)]} + e^{+i[\phi_a(\omega)-\phi_b(\omega)]}\}$$

Given the spectral separation criterion, the expression evaluates to 0 and hence the two gradient waveforms decouple.

$$=0\cdot\{e^{-i[\phi_a(\omega)-\phi_b(\omega)]} + e^{+i[\phi_a(\omega)-\phi_b(\omega)]}\}=0 \quad (50)$$

If there is spectral overlap ($A_a(\omega)A_b(\omega)\neq 0$), for those overlapping values of $\omega$, the phase term evaluates to 0 for the two gradients to decouple. This is equivalent to forcing:

$$e^{-i[\phi_a(\omega)-\phi_b(\omega)]} = -e^{+i[\phi_a(\omega)-\phi_b(\omega)]} \quad (51)$$

$$e^{-2i[\phi_a(\omega)-\phi_b(\omega)]} = -1 \quad (52)$$

The solution to this equation is the phase separation criterion, $$\phi_a - \phi_b = \pm \frac{\pi}{2} \quad (53)$$

again noting that $\phi$ that are $2\pi$ radians apart represent the same angle.

Multi-Dimensional Diffusion-Diffusion Correlation

The phase criteria imply that for any set of three (or more) diffusion gradients with mutual spectral overlap (e.g. $A_a(\omega)A_b(\omega)A_c(\omega)\neq 0$ for some $\omega$), they cannot mutually decouple. (Note that the background gradient in a diffusion-diffusion correlation experiment will also act like a third diffusion encoding gradient.) For them to each decouple with mutual overlap, consider a value of $\omega$, $\omega_0$, where each of the three overlap. For mutual decoupling to exist, then diffusion encoding gradients $g_a$ and $g_b$ decouple as well as the pair $g_a$ and $g_c$. Then $$\phi_a(\omega_0) - \phi_b(\omega_0) = \pm\frac{\pi}{2} \text{ and } \phi_a(\omega_0) - \phi_c(\omega_0) = \pm\frac{\pi}{2} \quad (54)$$

However this would imply that $$\phi_b(\omega_0) - \phi_c(\phi_0) = 0, \pi \quad (55)$$

meaning that the gradient waveforms $g_b$ and $g_c$ do not decouple.

Therefore, in order to decouple the diffusion encoding gradients, the spectra of the gradient waveforms can substantially overlap for at most two of the encoding gradient waveforms (FIGS. 36A to 36E). Separating out the spectra allows for multidimensional diffusion correlation experiments past two different diffusion dimensions. For example, strictly separating the spectra of each gradient waveform (FIG. 36B) will ensure decoupling. In some examples, letting pairs of gradient waveforms overlap with multiple other gradients, but with just two of them overlapping at a given frequency $\omega$ (FIGS. 36A, 36C, and 36D), can still maintain decoupling over many different gradient waveforms.

Background Gradient Cross-Terms and Diffusion-Diffusion Correlation

Figure 37A:
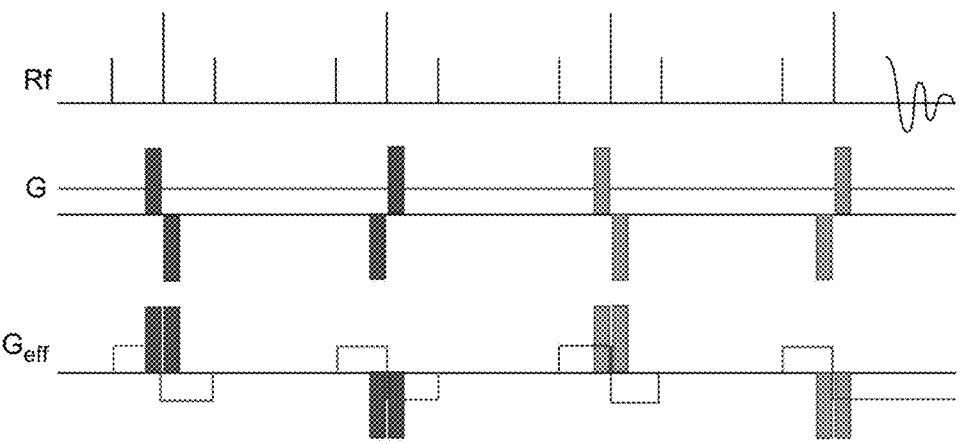
FIG. 37A shows minimization, via use of bi-polar gradient pulses, of background gradients on the general d-PFG, applied to a simulated echo based d-PFG sequence.
Figure 37B:
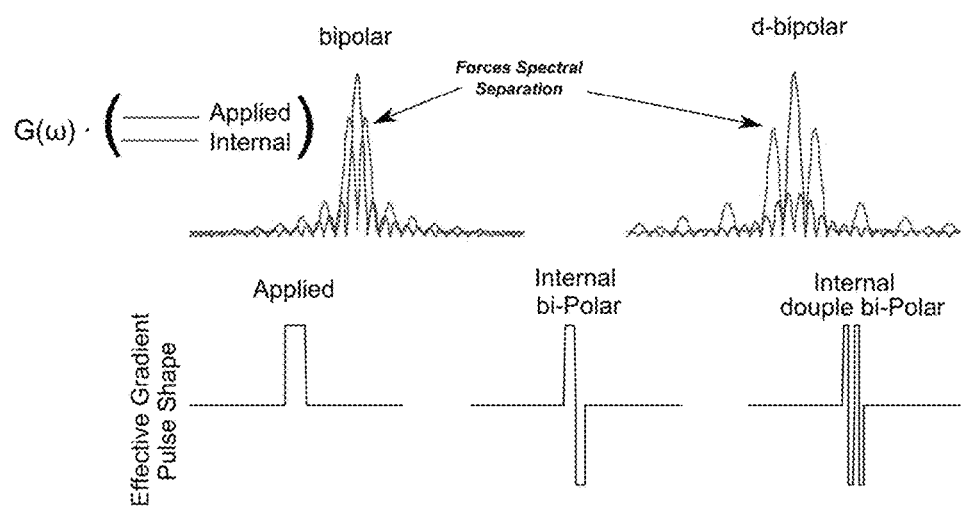
FIG. 37B shows plots of logarithms of the spectra of effective separated single gradient pulses and the corresponding background gradients showing the spectral separation.

Zheng et al. had previously identified that the spectral separation of a diffusion encoding gradient and the effective background gradient can be used to minimize the background gradient cross-term, but failed to generally identify conditions where overlap allows zeroing of this term. For example (FIG. 37A), the practice of using bi-polar gradient pulses in a stimulated echo d-PFG sequence achieves decoupling by flipping the sign midway of each gradient pulse while applying a 180 degree RF pulse. (N. Shemesh and Y. Cohen "Overcoming apparent Susceptibility-Induced Anisotropy (aSIA) by bipolar double-Pulsed-field-Gradient NMR." JMR 212 (2011) 362-369). The effect of this is to fix the spectra of the diffusion encoding gradient while pushing out the spectra of the internal gradients to higher frequencies (FIG. 37B). Including multiple such flips (FIG. 37B, d-bipolar), will further separate the effective gradients in terms of their spectra. What is established here is that for diffusion-diffusion correlation measurements, this property is used to minimize the signal cross-term between either the background gradient and a gradient waveform, or between two of the applied gradient waveforms in the presence of a background gradient in order to eliminate each of the cross-terms.

Orthogonalization

Two desired diffusion encoding gradients ($g_a(t)$, $g_b(t)$) will not necessarily decouple. For example, $g_1(t)$ and $g_2(t)$ in the d-PFG experiment (2803 in FIG. 26). However, a linear combination of these gradients ($g_\alpha(t)$, $g_\beta(t)$) can decouple; e.g.

$$\begin{bmatrix} g_\alpha(t) \\ g_\beta(t) \end{bmatrix} = M \begin{bmatrix} g_a(t) \\ g_b(t) \end{bmatrix} \quad (56)$$

where M is a real valued matrix:

$$M = \begin{bmatrix} m_{11} & m_{12} \\ m_{21} & m_{22} \end{bmatrix} \quad (57)$$

Returning to the d-PFG example, $$M = \begin{bmatrix} 1 & 1 \\ -1 & 1 \end{bmatrix} \quad (58)$$

and ($g_\alpha(t)$, $g_\beta(t)$) correspond to ($g_s(t)$, $g_d(t)$).

In this section, the criteria for the existence of an othogonalized combination and the formula to produce this decoupled pair are evaluated. Specifically, the orthogonalization criteria for $(g_a(t), g_b(t))$ is that the curve in 3-dimensional space parameterized by the Fourier transforms of the gradients:

$$\vec{c}(\omega) = \begin{bmatrix} |G_a(\omega)|^2 \\ |G_b(\omega)|^2 \\ \text{Re}(G_a(\omega)G_b^*(\omega)) \end{bmatrix} \tag{59}$$

lie in a plane. That is, referring FIG. 38A, each point in the curve $(\text{Re}(Q(\omega)), |G_1(\omega)|^2, |G_1(\omega)|^2)$ lies within a plane.

Given that the orthogonalization criterion is satisfied, the orthogonalization procedure may be applied. As the curve $\vec{c}(\omega)$ lies in a plane, there exists a vector $\vec{v}$ normal to it. This vector's elements relate to the elements in orthogonalization matrix as $$\vec{v} = s \begin{bmatrix} m_{11}m_{21} \\ m_{12}m_{22} \\ m_{11}m_{22} + m_{12}m_{21} \end{bmatrix} \tag{60}$$

where $$\vec{v} \cdot \vec{c}(\omega) = 0 \tag{61}$$

and s is any no-zero real valued scalar. This sets up a series of equations which can then be algebraically solved for a feasible solution matrix M, which can then be used to obtain $(g_\alpha(t), g_\beta(t))$ from $(g_a(t), g_b(t))$.

EXAMPLE

Figures 38A, 38B:
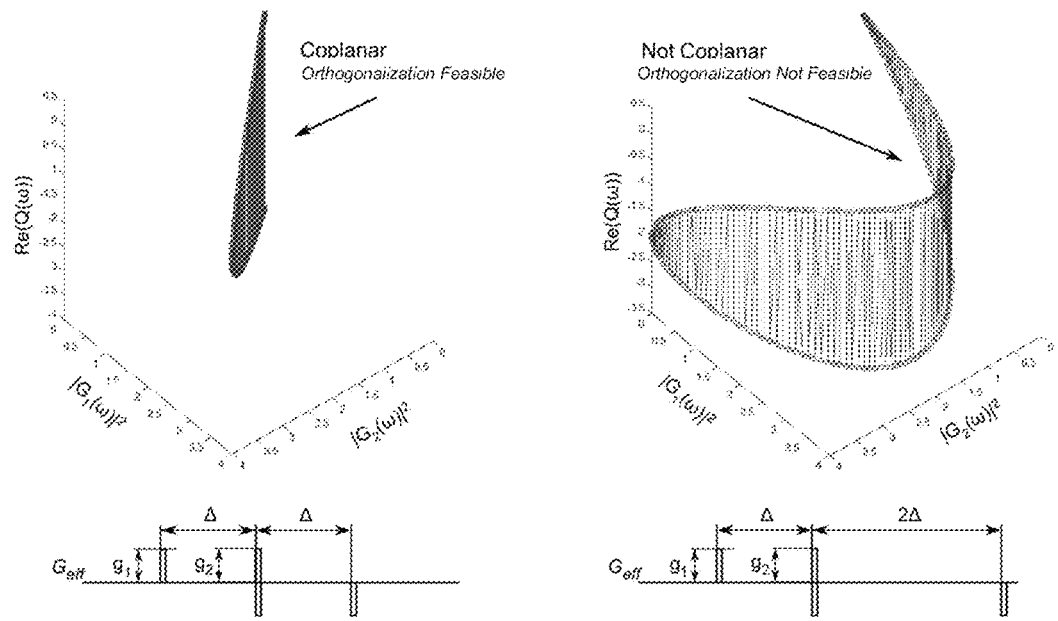
FIG. 38A shows the orthogonalization criteria for the $q_1/q_2$ pair with identical encoding times ($\Delta_1 = \Delta_2$).
FIG. 38B shows the orthogonalization criteria not being met for the d-PFG sequence with different encoding times ($\Delta_1 \neq \Delta_2$).

Referring to FIG. 38B, the curve defining the orthogonalization of the d-PFG encoding gradients $g_1(t)$ and $g_2(t)$ with identical encoding times and zero mixing time evaluates to $$\vec{c}_{q_{12}}(\omega) = \begin{bmatrix} 2[1 - \cos(2\Delta\omega)] \\ 2[1 - \cos(2\Delta\omega)] \\ 2\cos(\Delta\omega) - \cos(2\Delta\omega) - 1 \end{bmatrix} \tag{62}$$

Because the first two elements are identical, the curve they generate defines a line, and in combination with the third coordinate they define a plane in 3D space. Thus, this satisfies the orthogonalization criteria. For determining the orthogonalization vector, note that since the first two elements are identical and that they define a line, it is equivalent to make f) perpendicular to the curve $$\vec{c}(\omega) = \begin{bmatrix} 1 \\ 1 \\ f(\omega) \end{bmatrix} \tag{63}$$

Since $f(\omega)$ varies, the sole single vector that is in each instance perpendicular to $\vec{c}(\omega)$ is $$\vec{v} = a \begin{bmatrix} 1 \\ -1 \\ 0 \end{bmatrix}, \tag{64}$$

where a can be any non-zero real number. This normal vector sets up a series of algebraic equations to solve for the orthoganalization matrix.

$$m_{11}m_{21} = a \tag{65}$$

$$m_{12}m_{22} = -a \tag{66}$$

$$m_{11}m_{22} + m_{12}m_{21} = 0 \tag{67}$$

As expected, from knowledge of $q_s$ and $q_d$ in in examples described above, the matrix $$M = \begin{bmatrix} 1 & 1 \\ -1 & 1 \end{bmatrix}$$

solves this equation for $a = -1$. The general solution is $$M = \begin{bmatrix} \pm b & \pm b \\ \mp c & \pm c \end{bmatrix} \tag{68}$$

where $bc = a$. This expression still yields $(g_s(t), g_d(t))$ whose sole difference is the scaling of these two gradient shapes. Note that if $q_1$ and $q_2$ have different encoding times, $\Delta_1 \neq \Delta_2$, orthogonalization is not generally possible (see FIG. 38B).

To prove the orthogonalization condition and method, let the new gradient pair $(g_\alpha(t), g_\beta(t))$ be related to the original gradients $(g_a(t), g_b(t))$ by the matrix M. Then, $$g_\alpha = m_{11}g_a + m_{12}g_b \tag{69}$$

$$g_\beta = m_{21}g_a + m_{22}g_b \tag{70}$$

Applying the general decoupling criteria to $g_\alpha$, $g_\beta$ (Eq 30a), the following expression equals 0 for the gradient waveforms to decouple.

$$G_\alpha(\omega)G_\beta^*(\omega) + \tag{71}$$
$$G_\beta(\omega)G_\alpha^*(\omega) = [m_{11}G_a(\omega) + m_{12}G_b(\omega)][m_{21}G_a^*(\omega) + m_{22}G_b^*(\omega)] +$$
$$[m_{11}G_a^*(\omega) + m_{12}G_b^*(\omega)][m_{21}G_a(\omega) + m_{22}G_b(\omega)] \ldots =$$
$$m_{11}m_{21}|G_a(\omega)|^2 + m_{12}m_{22}|G_b(\omega)|^2 +$$
$$(m_{11}m_{22} + m_{12}m_{21})\text{Re}[G_a(\omega)G_b^*(\omega)]$$

This last expression can be written as the dot product of two vectors, one in terms of the matrix elements of M, and the other in terms of the Fourier transform of the initial gradient waveforms $(g_a(t), g_b(t))$. The decoupling criterion is then:

$$\begin{bmatrix} m_{11}m_{21} \\ m_{12}m_{22} \\ m_{11}m_{22} + m_{12}m_{21} \end{bmatrix} \cdot \begin{bmatrix} |G_a(\omega)|^2 \\ |G_b(\omega)|^2 \\ \text{Re}(G_a(\omega)G_b^*(\omega)) \end{bmatrix} = 0 \tag{72}$$

This is the equation of the orthogonalization procedure. The orthogonalization criteria, that $\vec{c}(\omega)$ lies in a plane, is needed for there to exist a non-trivial (non-zero) solution to this equation.

General Decoupling of Desired Diffusion Encoding Gradient Waveforms

This procedure can be used to take desired diffusion encoding gradient waveforms and a) determine if they can simply be combined (by forming linear combinations) to form a pair of decouple diffusion encoding gradients and b) determine the matrix formula for that pair.

Decoupling of the Same Gradient Profile Starting at Different Times

One of the ideas behind the d-PFG is to correlate a standard diffusion measurement at two subsequent times with an otherwise identical gradient waveform. Other measurements of diffusion (e.g. oscillating gradients) can similarly be correlated. However, as with the d-PFG, these gradient waveforms may not necessarily decouple. Since these gradient waveforms have the same shape and amplitude by construction, their power spectra ($|G_a(\phi)|^2$, $|G_b(\phi)|^2$) are identical. As with the d-PFG example, it is equivalent to find the vector orthogonal to the curve:

$$\vec{c}(\omega) = \begin{bmatrix} 1 \\ 1 \\ f(\omega) \end{bmatrix}, \quad (73)$$

and the solution for the orthogonalization matrix is again $$M = \begin{bmatrix} 1 & 1 \\ -1 & 1 \end{bmatrix}.$$

Thus the sum and difference ("$q_s$" "$q_d$") of correlating the same diffusion measurement at different times will in any event form a decoupled pair of diffusion encoding gradients.

Figure 39:
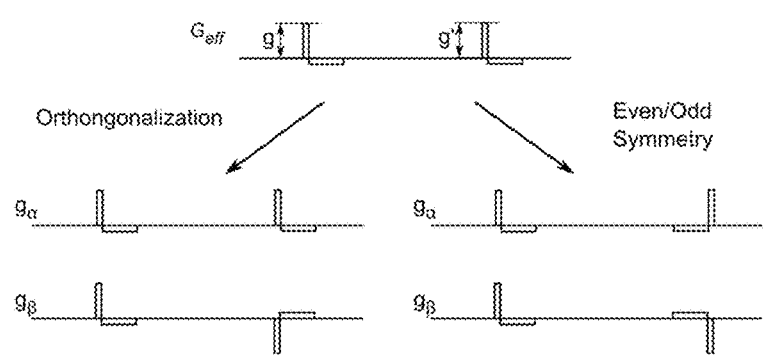
FIG. 39 shows the construction of decoupled gradient waveforms given the orthogonalization criteria/method and compares their construction to the odd/even criteria/method.

Referring to FIG. 39, this procedure is distinct from utilizing the odd/even rule to combine the gradients to make decoupled pairs. If for the diffusion measurement being correlated the corresponding gradient waveform, g(t), is asymmetric, then the resulting ($g_\alpha(t)$, $g_\beta(t)$) from it will also be asymmetric as shown in the lower left portion of FIG. 39. However, by the orthogonalization procedure, it is still known that these are decoupled. This is distinct from the sorts of modifications that could be made to the gradient waveform which, referring to the lower right portion of FIG. 39, would allow the use of the odd/even criteria.

Example Implementations

Figure 40:
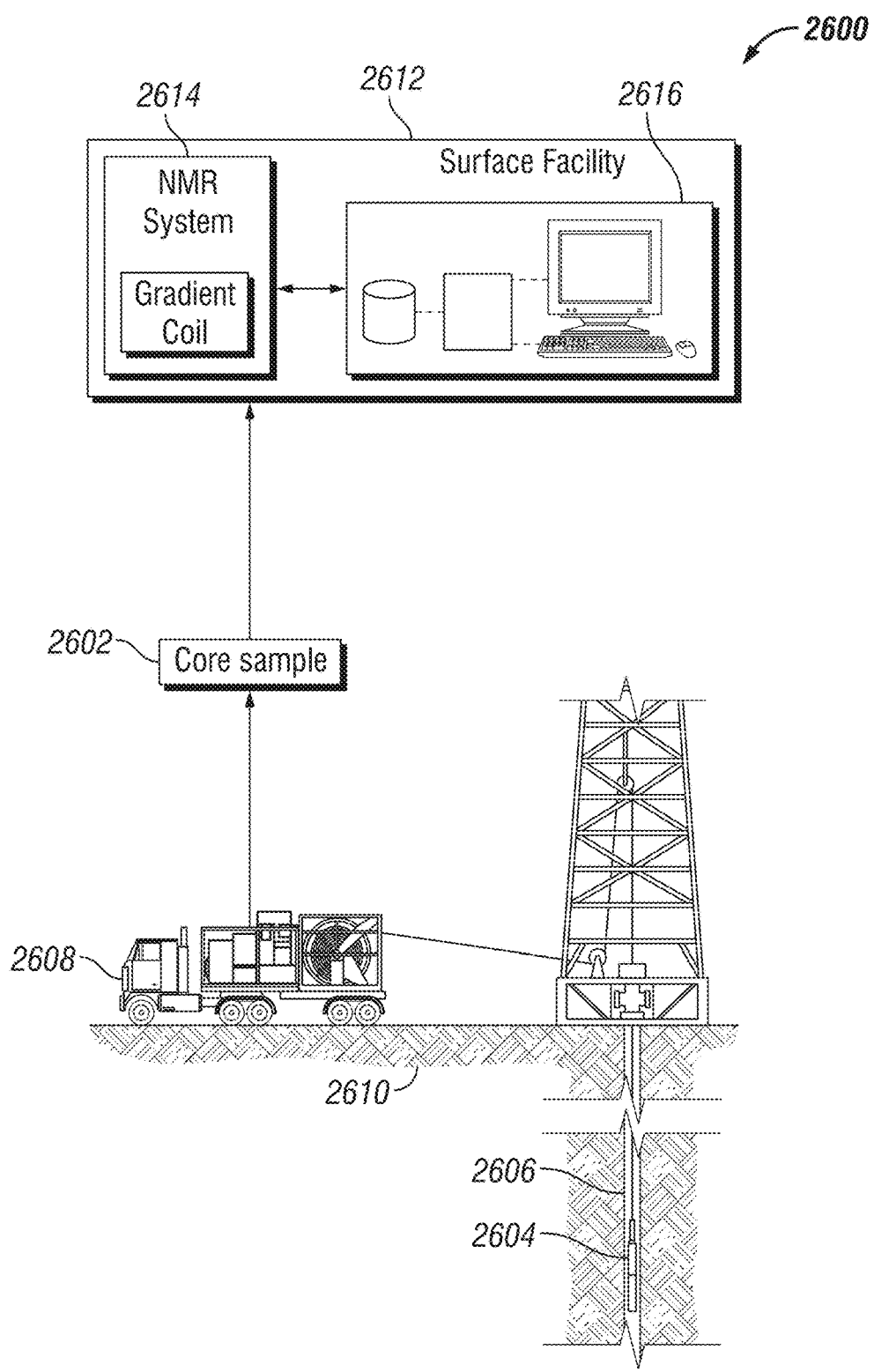
FIG. 40 shows a rock core system for determining properties of a rock core sample.

FIG. 40 shows a rock core system 2600 for determining properties of a rock core sample 2602. The system 2600 includes a wireline tool string 2604 that is deployed in a well 2606 via a wireline truck 2608. The wireline tool 2604 is a downhole tool adapted to remove the core sample 2602 from a formation 2610. Once the core sample 2602 is obtained, the core is transported to a surface facility 2612, which includes an NMR system 2614 and operator module 2616 for carrying out the methods and processes described herein, as well as other processing. According to some embodiments, the surface facility 2612 may be located in a location remote from the well 2606.

The operator module 2616 includes a computer system (e.g., a processor and a memory) that supports a graphical user interface (GUI), such as a monitor, a touch screen, a mouse, a keyboard and/or a joystick. The GUI allows an operator to control and communicate with the NMR system 2614. The NMR system 2614 may include a gradient element 2618 for applying pulsed field gradient pulses to the core sample 2602 (e.g., a gradient insert). In various embodiments, the gradient element 2618 is a metal wound coil. The NMR system 2614 includes a corresponding electrical power supply to inject electrical current into the coil. The gradient coil may be designed with a particular geometry so that the magnetic field produced by the coil spatially varies over the sample. The spatial variation may be designed to have a constant gradient along a particular direction. This direction is referred to herein as "a gradient direction." In illustrative embodiments, three sets of such gradient coils are provided along three gradient directions (e.g., the Cartesian coordinates—x, y, and z) in order to provide imaging in three dimensions, such as in a medical MRI application. Other NMR systems may be equipped with one or two such gradient coil sets so that spatial resolution can be achieved along 1 or 2 directions.

In one specific embodiment, the rock core system 2600 is used to analyze a water flooded rock core sample (e.g., initially oil saturated) 2602. The rock core sample 2602 is removed from the formation 2610 using the wireline tool 2604. The rock core sample 2602 is placed into the NMR system 2614. In this case, the NMR system 2614 includes a single z-axis gradient coil. A pulse sequence is applied to the rock core sample 2602 using the NMR system 2614. The pulse sequence includes two sets of gradient pulses followed by a CPMG acquisition to encode for $T_2$ relaxation time. The sequence is repeated and $q_{sz}$ and $q_{dz}$ are incremented over a two-dimensional $q_s$ and $q_d$ Cartesian array for each acquisition to obtain NMR signal data. A three-dimensional inverse Laplace transform is performed to convert the NMR data into a three-dimensional plot of $D_s$, $D_d$, and $T_2$ relaxation time. Peaks are identified within the three-dimensional plot (e.g., water, oil). In the case of light oils, water in small pores with a similar apparent diffusion coefficient and $T_2$ to the oil are now separated in the $D_s$ and $D_d$ plane. In some embodiments, the $D_s$ and $D_d$ plot can be converted into a bulk diffusion coefficient ($D_0$) and surface-to-volume ratio (S/V) plot by converting each $D_s$ and $D_d$ coordinate into $D_0$ and S/V coordinates via equations (10) and (11). As explained above, the equations use the short time diffusion approximation. Other equations can also be used. Fluid type and pore size of the rock core sample 2602 may then be identified based on NMR signal position on these axes. The $T_2$ relaxation time may then identify spines in pores too small or large to be characterized by the $D_s$ and $D_d$ measurement.

In another example, the rock core system 2600 is used to analyze a cleaned brine saturated rock core sample 2602. The rock core sample 2602 is analyzed to determine a three-dimensional plot of $D_s$, $D_d$, and $T_2$ relaxation time. The $D_s$ and $D_s$ axes can be converted into bulk diffusion coefficient ($D_0$) and surface-to-volume ratio (S/V) axes using equations (10) and (11), as explained above. This plot relates the values of the surface-to-volume ratio to respective values of $T_2$ relaxation time. The surface-to-volume ratio and the $T_2$ relaxation time values are related a surface relaxivity of the pores according to the following relationship.

$$\frac{1}{T_2} = \frac{1}{T_{2,bulk}} + \rho \frac{S}{V} \tag{74}$$

where $T_2$ is the measured $T_2$ relaxation time, $T_{2,bulk}$ is the $T_2$ relaxation time for the fluid in a bulk environment, and p is the surface relaxivity of the pores. The relationship between the surface-volume-ratio and the $T_2$ relaxation time can be determined by plotting the two values. A relationship that varies indicates that pores of different sizes have different pore surface properties.

Figure 41:
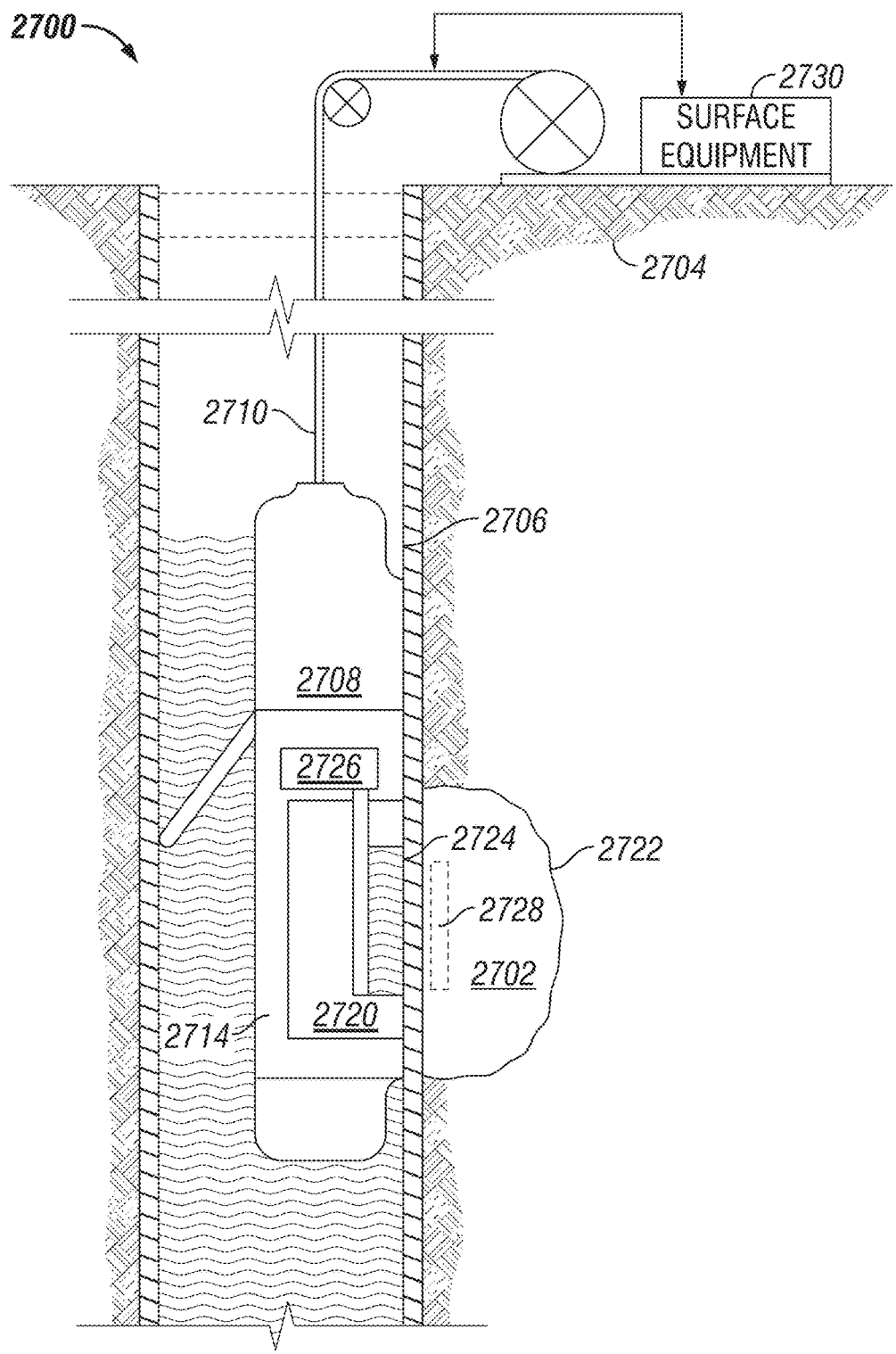
FIG. 41 shows a wireline system for determining properties of an earth formation.

FIG. 41 shows a wireline system 2700 for determining properties of an earth formation. The wireline system 2700 is used to investigate, in situ, a substance 2702 within the earth formation 2704 surrounding a wellbore 2706 to determine a property of the substance. As shown in FIG. 41, a wireline tool 2708 is disposed within the wellbore 2706 and suspended on an armored cable 2710. Although the wireline tool 2708 is shown as a single body in FIG. 41, the tool may include separate bodies. As shown in FIG. 41, the wireline tool 2708 includes an NMR logging module 2714 that is used to apply NMR pulse sequences to the formation 2704. The NMR logging module 2714 includes an electro-magnetic device 2720 for applying a static magnetic field to a sensitivity zone 2722 within the earth formation 2704. In some embodiments, the electro-magnetic device 2720 is a magnet or an array of magnets formed from a magnetic material. The NMR logging module 2714 also includes at least one coil 2724 and NMR electronics 2726 electronically coupled to the coil. The coil 2724 and NMR electronics 2726 apply an oscillating field to an area of interest 2728 within the earth formation 2704. The area of interest 2702 is located within the sensitivity zone 2722 of the electro-magnetic device 2720. In accordance with various embodiments of the present disclosure, the oscillating field applied to the earth formation 2704 includes the NMR pulse sequences described above. In various embodiments, the wireline tool 2708 does not include a gradient coil. In such embodiments, an effective pulsed field gradient is produced by the two sets of pulses or other form of pulses, e.g., waveform pulses. FIG. 18 shows an example of an NMR pulse sequence that produces an effective pulsed field gradient. In some examples, the NMR pulse sequences are repeated for a selected range of $q_s$ and $q_d$ by choosing corresponding values of $\delta_1$ and $\delta_2$, as described with respect to FIGS. 17 and 18. The NMR signal data produced by the sequences described herein is detected using the coil 2724 and used to analyze the formation using the methods and processes described above. The wireline system 2700 also includes surface equipment 2730 for supporting the wireline tool 2708 within the wellbore 2706. In various embodiments, the surface equipment 2730 includes an operator interface for communicating with the NMR logging module 2714. Such an operator interface has already been described with reference to FIG. 40. In some embodiments, the NMR logging module 2714 and operator module communicate through the armored cable 2710.

The NMR systems and methods described herein are not limited to any device type or system. The NMR systems and methods described herein can be implemented in surface environments, such as a laboratory. The systems and methods described herein are also not limited to application in any type of particular field. For example, the systems and methods can be used to analyze biological tissues, such as bone tissue or brain tissue. Many biological tissues include porous media and characterization of the microstructure, the pore sizes, and the intrinsic diffusion coefficient of tissues is useful in the field of clinical medicine. The systems and methods described herein can be applied to the study such tissue structure and can be combined with MRI for clinical use.

With respect to wellbore applications, the NMR systems and methods described herein are not limited to wireline systems, such as the one shown in FIG. 41. For example, illustrative embodiments can also be used with any suitable means of conveyance, such coiled tubing. Various embodiments of the present disclosure may also be applied in logging-while-drilling (LWD) systems (e.g., a LWD tool) or measuring-while-drilling systems (e.g., MWD tools).

The processes described herein, such as, for example, (1) applying NMR pulse sequences to a substance, (2) acquiring an array of NMR signal data for $q_s$ and $q_d$ values, (3) determining properties of the substance using the array of NMR signal data, (4) performing an inverse Laplace transform on the array of NMR signal data to determine a plot diffusion coefficients, (5) identifying peaks within the plot, (6) determining a bulk diffusion coefficient of the substance using the plot, (7) determining a surface-to-volume ratio of the substance using the plot, and (8) determining and generating a decoupled gradient waveform (distinct encoding modes), can be performed and implemented at least in part by a computer system.

The term "computer system" should not be construed to limit the embodiments disclosed herein to any particular device type or system. The computer system may be a laptop computer, a desktop computer, or a mainframe computer. The computer system may also include a computer processor (e.g., a microprocessor, microcontroller, digital signal processor or general purpose computer) for executing any of the methods and processes described above (e.g., processes (1)-(8)). The computer system may further include a memory such as a semiconductor memory device (e.g., a RAM, ROM, PROM, EEPROM, or Flash-Programmable RAM), a magnetic memory device (e.g., a diskette or fixed disk), an optical memory device (e.g., a CD-ROM), a PC card (e.g., PCMCIA card), or other memory device. This memory may be used to store, for example, the NMR pulse sequences and acquired NMR signal data, as described above.

Any of the methods and processes described above, including processes (1)-(8) as listed above, can be implemented as computer program logic for use with the computer processor. The computer program logic may be embodied in various forms, including a source code form or a computer executable form. Source code may include a series of computer program instructions in a variety of programming languages (e.g., an object code, an assembly language or a high-level language such as C, C++ or JAVA). Such computer instructions can be stored in a non-transitory computer readable medium (e.g., memory) and executed by the computer processor. For example, the NMR pulse sequences described herein may be implemented as a series of computer instructions that define the characteristics of at least some of the NMR pulse sequences described herein (e.g., pulse amplitude, pulse phase, pulse duration, first area parameter, second area parameter, and diffusion times ($\Delta$ and $2\Delta$)). The computer instructions may be distributed in any form as a removable storage medium with accompanying printed or electronic documentation (e.g., shrink wrapped software), preloaded with a computer system (e.g., on system ROM or fixed disk), or distributed from a server or electronic bulletin board over a communication system (e.g., the Internet or World Wide Web).

Although several example embodiments have been described in detail above, those skilled in the art will readily appreciate that many modifications are possible in the example embodiments without materially departing from the scope of this disclosure. Accordingly, any such modifications are intended to be included within the scope of this disclosure.

The invention claimed is:

1. A method comprising:
applying a nuclear magnetic resonance (NMR) pulse sequence using a nuclear magnetic resonance (NMR) system, the pulse sequence comprising a first set of pulses and a second set of pulses to a substance, wherein the first set of pulses encode for a first diffusion time and the second set of pulses encode for a second diffusion time, the first diffusion time overlapping the second diffusion time;
detecting, using the NMR system, a NMR signal produced by the NMR pulse sequence to obtain NMR signal data;
applying to the substance a modified NMR pulse sequence generated by changing at least one of (a) the first diffusion time and (b) the second diffusion time;
detecting a NMR signal produced by the modified NMR pulse sequence to obtain NMR signal data;
determining a property of the substance using at least the NMR signal data over each of the overlapping diffusion times for the NMR pulse sequence and the modified NMR pulse sequence; and
providing the property at a computing system.

2. The method of claim 1, wherein at least one of the first set of pulses and the second set of pulses is comprised of a waveform pulse.

3. The method of claim 1, wherein at least one of the first set of pulses and the second set of pulses is comprised of rectangular pulses.

4. The method of claim 1, wherein the NMR pulse sequence is comprised of a continuous waveform that includes the first set of pulses and the second set of pulses.

5. The method of claim 1, wherein the first set of pulses is comprised of a waveform pulse and the second set of pulses is comprised of a rectangular pulse.

6. The method of claim 1, wherein
(i) the first set of pulses comprises two pulses that are each defined by a first area parameter and separated by a time period, and
(ii) the second set of pulses comprises two pulses that are each defined by a second area parameter and separated by the time period.

7. The method of claim 6, further comprising:
applying the NMR pulse sequence to the substance a plurality of times using different values for the first area parameter and the second area parameter;
detecting NMR signals produced by the NMR pulse sequence for the different values of the first area parameter and the second area parameter to obtain NMR signal data.

8. The method of claim 6, wherein the values of the first area parameter and the second area parameter are varied according to the following relationships:

$$q_s = q_1 + q_2,$$

$$q_d = q_2 - q_1,$$

where $q_1$ is the first area parameter, $q_2$ is the second area parameter, $q_s$ is an area parameter for the portion of pulses that correspond to the first diffusion time, and $q_d$ is an area parameter for the complimentary portion of pulses that correspond to the second diffusion time.

9. The method of claim 8, further comprising:
performing a Laplace inversion on the NMR signal data to obtain diffusion coefficients for the first diffusion time and the second diffusion time.

10. The method of claim 1, wherein the substance is a porous medium containing a fluid.

11. The method of claim 10, wherein the substance is a rock core containing oil, water, or both.

12. The method of claim 11, further comprising: removing the rock core from a formation.

13. The method of claim 10, wherein the property is (i) a bulk diffusion coefficient for the fluid, (ii) a surface-to-volume ratio for the porous medium, or (iii) both.

14. The method of claim 1, wherein the first set of pulses and the second set of pulses comprise pulsed field gradient pulses.

15. The method of claim 14, wherein the pulsed field gradient pulses are applied to the substance using a gradient coil.

16. The method of claim 1, wherein a constant field gradient is applied to the substance and the first set of pulses and the second set of pulses are radio frequency pulses that produce an effective pulsed field gradient within the substance.

17. The method of claim 6, wherein
(i) the two pulses within the first set of pulses include pulse areas that cancel, and
(ii) the two pulses within the second set of pulses include pulse areas that cancel.

18. The method of claim 1, wherein the substance is a fluid within an underground formation and the NMR sequence is applied to the fluid using a NMR logging tool.

19. The method of claim 1, wherein a time period between the first set of pulses and the second set of pulses is less than the two overlapping diffusion times.

20. A system for determining a property of a substance, the system comprising:
a nuclear magnetic resonance (NMR) system for applying NMR pulse sequences to a substance and detecting NMR signals generated by the substance to obtain NMR signal data;
a processor; and
a memory storing instructions executable by the processor to perform processes that include:
providing an NMR pulse sequence to the NMR system, the NMR pulse sequence comprising a first set of pulses and a second set of pulses, wherein the first set of pulses encode for a first diffusion time and the second set of pulses encode for a second diffusion time, the first diffusion time overlapping the second diffusion time;
determining a correlation in the NMR signal data with respect to the first diffusion time and the second diffusion time; and
determining the property of the substance using the NMR signal data over each of the overlapping diffusion times.

* * * * *